(12) United States Patent
Breyen et al.

(10) Patent No.: US 7,110,240 B2
(45) Date of Patent: Sep. 19, 2006

(54) IMPLANTABLE MEDICAL DEVICE HAVING FLAT ELECTROLYTIC CAPACITOR WITH DIFFERING SIZED ANODE AND CATHODE LAYERS

(75) Inventors: Mark D. Breyen, Plymouth, MN (US); Andrew Michael Jacobs, Eden Prairie, MN (US); Anthony W. Rorvick, Brooklyn Park, MN (US); Paul A. Pignato, Stacy, MN (US)

(73) Assignee: Medtronic, Inc., Minneapolis, MN (US)

( * ) Notice: Subject to any disclaimer, the term of this patent is extended or adjusted under 35 U.S.C. 154(b) by 23 days.

(21) Appl. No.: 11/196,142

(22) Filed: Aug. 3, 2005

(65) Prior Publication Data
US 2005/0264979 A1 Dec. 1, 2005

Related U.S. Application Data

(63) Continuation of application No. 10/918,061, filed on Aug. 13, 2004, now Pat. No. 6,963,482, which is a continuation-in-part of application No. 09/531,352, filed on Mar. 20, 2000, now Pat. No. 6,678,559.

(51) Int. Cl.
*H01G 4/35* (2006.01)

(52) U.S. Cl. .............. 361/302; 361/516; 361/532; 607/5

(58) Field of Classification Search ............... 361/302, 361/303, 508, 516, 528–529, 509; 607/4, 607/5, 36; 29/25.03
See application file for complete search history.

(56) References Cited

U.S. PATENT DOCUMENTS 6,009,348 A * 12/1999 Rorvick et al. ............... 607/5
6,459,566 B1 * 10/2002 Casby et al. ................ 361/517

* cited by examiner

*Primary Examiner*—Anthony Dinkins
(74) *Attorney, Agent, or Firm*—Carol F. Barry; Girma Wolde-Michael

(57) ABSTRACT

A capacitor is described. The capacitor includes a case chamber. An electrode stack assembly is disposed within the case chamber. The electrode stack assembly includes a layer. The layer includes an anode subassembly. The anode subassembly comprises at least one anode layer that has an anode edge disposed at a first distance from an interior wall of the case chamber. The layer also includes a capacitor layer. The capacitor layer includes a cathode edge disposed at a second distance from the wall interior. The second distance is greater than the first distance.

1 Claim, 20 Drawing Sheets $$\frac{\Delta T}{T} \leqslant 0.1,\ 0.05,\ 0.15,\ 0.20,\ 0.25,\ 0.30,\ 0.35,\ 0.40,\ 0.45,\ \text{or}\ 0.50$$

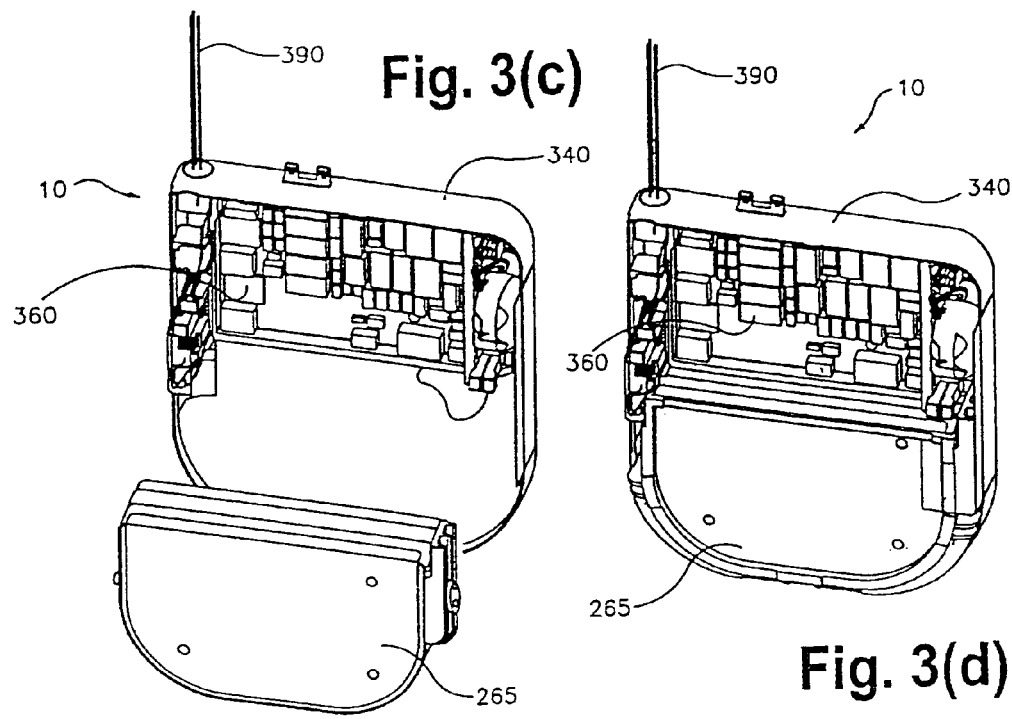
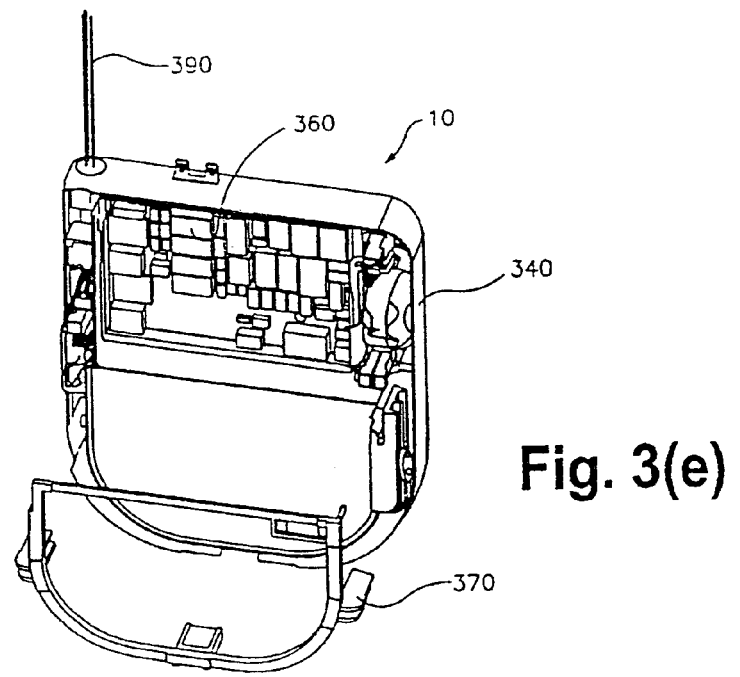

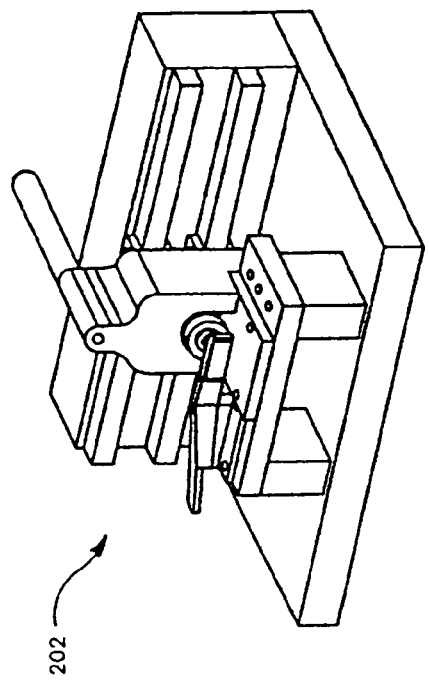
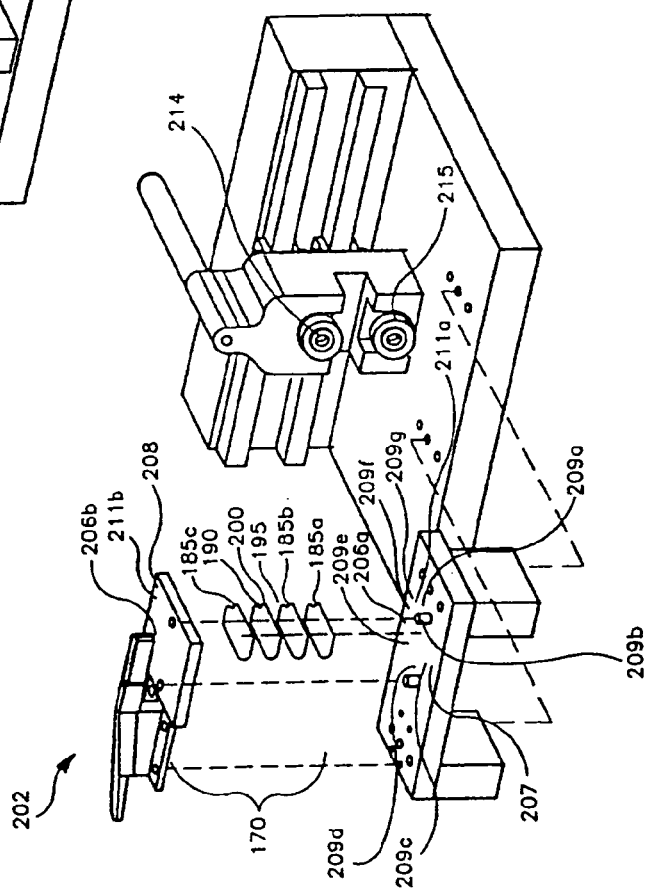
FIG. 5(b)
FIG. 5(a)

$$\frac{\Delta T}{T} \leq 0.1, \ 0.05, \ 0.15, \ 0.20, \ 0.25, \ 0.30, \ 0.35, \ 0.40, \ 0.45, \text{ or } 0.50$$

$\frac{\Delta T}{T} \leq$ 0.1, 0.05, 0.15, 0.20, 0.25, 0.30, 0.35, 0.40, 0.45, or 0.50

IMPLANTABLE MEDICAL DEVICE HAVING FLAT ELECTROLYTIC CAPACITOR WITH DIFFERING SIZED ANODE AND CATHODE LAYERS

RELATED APPLICATION

This application is a continuation application of prior U.S. patent application Ser. No. 10/918,061, filed Aug. 13, 2004, entitled Implantable Medical Device Having Flat Electrolytic Capacitor with Differing Sized Anode and Cathode Layers", now U.S. Pat. No. 6,963,482.

This application is a continuation-in-part of U.S. patent application Ser. No. 09/531,352 filed Mar. 20, 2000, now U.S. Pat. No. 6,678,559 in the names of Mark D. Breyen et al., and entitled IMPLANTABLE MEDICAL DEVICE HAVING A CAPACITOR ASSEMBLY WITH LINER.

FIELD OF THE INVENTION

This invention relates to implantable medical devices (IMDs) and their various components, including flat electrolytic capacitors for same, and methods of making and using same, particularly to an electrode stack assembly comprising a plurality of stacked capacitor layers each comprising an anode sub-assembly of at least one anode layer, a cathode layer and separator layers wherein the anode and cathode layers have differing dimensions that avoid electrical short circuits between peripheral edges of adjacent anode and cathode layers.

BACKGROUND OF THE INVENTION

A wide variety of IMDs are known in the art as described in the above-referenced parent application Ser. No. 09/531,352, and the provisional application that it claims priority from, and in commonly assigned U.S. Pat. No. 6,006,133. Of particular interest are implantable cardioverter-defibrillators (ICDs) that deliver relatively high energy cardioversion and/or defibrillation shocks to a patient's heart when a malignant tachyarrhythmia, e.g., atrial or ventricular fibrillation, is detected. Current ICDs typically possess single or dual chamber pacing capabilities for treating specified chronic or episodic atrial and/or ventricular bradycardia and tachycardia and were referred to previously as pacemaker/cardioverter/defibrillators (PCDs). Earlier developed automatic implantable defibrillators (AIDs) did not have cardioversion or pacing capabilities. For purposes of the present invention ICDs are understood to encompass all such IMDs having at least high voltage cardioversion and/or defibrillation capabilities.

Generally speaking, it is necessary to employ a DC-DC converter within an ICD implantable pulse generator (IPG) to convert electrical energy from a low voltage, low current, electrochemical cell or battery enclosed within the IPG housing to a high voltage energy level stored in one or more high energy storage capacitor, as shown for example, in commonly assigned U.S. Pat. No. 4,548,209. The conversion is effected upon confirmation of a tachyarrhythmia by a DC-DC "flyback" converter which includes a transformer having a primary winding in series with the battery and a secondary winding in series with the high energy capacitor(s) and an interrupting circuit or switch in series with the primary coil and battery that is periodically opened and closed during a charging cycle. Charging of the high energy capacitor is accomplished by inducing a voltage in the primary winding of the transformer creating a magnetic field in the secondary winding when the switch is closed. The field collapses when the current in the primary winding is interrupted by opening the switch, and the collapsing field develops a current in the secondary winding which is applied to the high energy capacitor to charge it. The repeated interruption of the supply current charges the high energy capacitor to a desired level of several hundred volts over a charging time of the charge cycle. Then, the energy is rapidly discharged from the high voltage capacitor(s) through cardioversion/defibrillation electrodes coupled to the IPG through ICD leads and arranged about or in a heart chamber or vessel if the tachyarrhythinia is confirmed as continuing at the end of the charge time. The cardioversion/defibrillation shocks effected by discharge of such capacitors are typically in the range of about 25 to 40 Joules. The process of delivering cardioversion/defibriflation shocks in this way may be repeated if an earlier delivered cardioversion/defibrillation shock does not convert the tachyarrhythmia to a normal heart rhythm.

Energy, volume, thickness and mass are critical features in the design of ICD pulse generators that are coupled to the ICD leads. The battery(s) and high voltage capacitor(s) used to provide and accumulate the energy required for the cardioversion/defibrillation shocks have historically been relatively bulky and expensive. Presently, ICD IPGs typically have a volume of about 40 to about 60 cc, a thickness of about 13 mm to about 16 mm and a mass of approximately 100 grams.

It is desirable to reduce the volume, thickness and mass of such capacitors and ICD IPGs without reducing deliverable energy. Doing so is beneficial to patient comfort and minicizes complications due to erosion of tissue around the ICD IPG. Reductions in size of the capacitors may also allow for the balanced addition of volume to the battery, thereby increasing longevity of the ICD IPG, or balanced addition of new components, thereby adding functionality to the ICD IPG. It is also desirable to provide such ICD IPGs at low cost while retaining the highest level of performance. At the same time, reliability of the capacitors cannot be compromised.

Various types of flat and spiral-wound capacitors are known in the art, some examples of which are described as follows and/or may be found in the patents listed in Table 1 of the above-referenced parent patent application Ser. No. 09/531,352.

Prior art high voltage electrolytic capacitors used in ICDs have two or more anode and cathode layers (or "electrodes") and operate at room or body temperature. Typically, the capacitor is formed with a capacitor case enclosing an etched aluminum foil anode, an aluminum foil or film cathode, and a Kraft paper or fabric gauze spacer or separator impregnated with a solvent based liquid electrolyte interposed therebetween. A layer of aluminum oxide that functions as a dielectric layer is formed on the etched aluminum anode, preferably during passage of electrical current through the anode. The electrolyte comprises an ion producing salt that is dissolved in a solvent and provides ionic electrical conductivity between the cathode and the aluminum oxide dielectric. The energy of the capacitor is stored in the electrostatic field generated by opposing electrical charges separated by the aluminum oxide layer disposed on the surface of the anode and is proportional to the surface area of the aluminum anode. Thus, to minimize the overall volume of the capacitor one must maximize anode surface area per unit volume without increasing the capacitor's overall (i.e., external) dimensions. The separator material, anode and cathode layer terminals, internal packaging, electrical interconnections, and alignment features and cathode material further increase the thickness and volume of a capacitor. Consequently, these and other components in a capacitor and the desired capacitance limit the extent to which its physical dimensions may be reduced.

Some ICD IPGs employ commercial photoflash capacitors similar to those described by Troup in "Implantable Cardioverters and Defibrillators," *Current Problems in Cardiology*, Volume XIV, Number 12, December 1989, Year Book Medical Publishers, Chicago, and as described in U.S. Pat. No. 4,254,775. The electrodes or anode and cathodes are wound into anode and cathode layers separated by separator layers of the spiral. Anode layers employed in such photoflash capacitors typically comprise one or two sheets of a high purity (99.99%), porous, highly etched, anodized aluminum foil. Cathode layers in such capacitors are formed of a non porous, highly etched aluminum foil sheet which may be somewhat less pure (99.7%) respecting aluminum content than the anode layers. The separator formed of one or more sheet or layer of Kraft paper saturated and impregnated with a solvent based liquid electrolyte is located between adjacent anode and cathode layers. The anode foil thickness and cathode foil thickness are on the order of 100 micrometers and 20 micrometers, respectively. Most commercial photoflash capacitors contain a core of separator paper intended to prevent brittle, highly etched aluminum anode foils from fracturing during winding of the anode, cathode and separator layers into a coiled configuration. The cylindrical shape and paper core of commercial photoflash capacitors limits the volumetric packaging efficiency and thickness of an ICD IPG housing made using same.

The aluminum anodes and cathodes of aluminum electrolytic capacitors generally each have at least one tab extending beyond their perimeters to facilitate electrical connection of all (or sets of) the anode and cathode layers electrically in parallel to form one or more capacitor and to make electrical connections to the exterior of the capacitor case. Tab terminal connections for a wound electrolytic capacitor are described in U.S. Pat. No. 4,663,824 that are laser welded to feedthrough pin terminals of feedthroughs extending through the case. Wound capacitors usually contain two or more tabs joined together by crimping or riveting.

Flat electrolytic capacitors have also been disclosed in the prior art for general applications as well as for use in ICDs. More recently developed ICD IPGs employ one or more flat high voltage capacitor to overcome some of the packaging and volume disadvantages associated with cylindrical photoflash capacitors. For example, U.S. Pat. No. 5,131,388 discloses a flat capacitor having a plurality of stacked capacitor layers each comprising an "electrode stack subassembly". Each capacitor layer contains one or more anode sheet forming an anode layer having an anode tab, a cathode sheet or layer having a cathode tab and a separator for separating the anode layer from the cathode layer. In the '388 patent, the capacitor stack of stacked capacitor layers is encased within a non-conductive, polymer envelope that is sealed at its seams and fitted into a chamber of a conductive metal, capacitor case or into a compartment of the ICD IPG housing, and electrical connections with the capacitor anode(s) and cathode(s) are made through feedthroughs extending through the case or compartment wall. The tabs of the anode layers and the cathode layers of all of the capacitor layers of the stack are electrically connected in parallel to form a single capacitor or grouped to form a plurality of capacitors. The aluminum anode layer tabs are gathered together and electrically connected to a feedthrough pin of an anode feedthrough extending through the case or compartment wall. The aluminum cathode layer tabs are gathered together and electrically connected to a feedthrough pin of a cathode feedthrough extending through the case or compartment wall or connected to the electrically conductive capacitor case wall.

Many improvements in the design of flat aluminum electrolytic capacitors for use in ICD IPGs have been disclosed, e.g., those improvements described in "High Energy Density Capacitors for Implantable Defibrillators" presented by P. Lunsmann and D. MacFarlane at *CARTS 96: 16th Capacitor and Resistor Technology Symposium*, 11–15 Mar. 1996, and at *CARTS-EUROPE 96: 10th European Passive Components Symposium*, 7–11 Oct. 1996, pp. 35–39. Further features of flat electrolytic capacitors for use in ICD IPGs are disclosed in U.S. Pat. Nos. 4,942,501; 5,086,374; 5,146,391; 5,153,820; 5,562,801; 5,584,890; 5,628,801; and 5,748,439, all issued to MacFarlane et al.

A number of recent patents including U.S. Pat. No. 5,660,737 and U.S. Pat. Nos. 5,522,851; 5,801,917; 5,808,857; 5,814,082; 5,908,151; 5,922,215; 5,926,357; 5,930,109; 5,968,210 and 5,983,472, all assigned to the same assignee, disclose related flat electrolytic capacitor designs for use in ICDs. In several of these patents, internal alignment elements are employed as a means for controlling the relative edge spacing of the anode and cathode layers from the conductive capacitor case. In these patents, each anode layer and cathode layer is provided with an outwardly extending tab, and the anode and cathode tabs are electrically connected in common to a feedthrough pin and a step feature of the conductive capacitor case, respectively. The cathode tabs are gathered together against the step feature and ultrasonically welded together and to the step feature. In the '357 patent, the anode tabs are laser welded to one end of an aluminum ribbon that is ultrasonically welded at its other end to an aluminum layer that is ultrasonically welded to the terminal pin. The feedthrough terminal pin is electrically isolated from and extends outside and away from the case to provide an anode connection pin. A cathode connection pin is attached to the case and extends outwardly therefrom. The anode and cathode connection pins are electrically connected into the DC-DC converter circuitry, but the attachment mechanism is not described in any detail.

Thus, the anode layers and the cathode layers of each capacitor layer in the stack are electrically coupled together to form one or more capacitor cathode and anode. In assembling a capacitor of these types, it is necessary that the anode and cathodes remain separated electrically from one another by the separators placed between adjoining cathode and anode layers to prevent short circuiting. It is also important that a minimum separation between the anode and cathode layers be maintained to prevent arcing therebetween, or between an anode layer of the anode and the case, when the case is conductive and coupled to the cathode. In cylindrical capacitors, such spacing is typically maintained at the electrode edges or peripheries by providing separator overhang at the top and bottom of the anode and cathode winding. In commercial cylindrical capacitors, the amount of separator overhang is typically on the order of 0.050 to 0.100 inches (0.127 to 0.254 mm). In addition, the anode and cathode are aligned precisely and coiled tightly to prevent movement of the anode, cathode and separator during subsequent processing and use.

In flat electrolytic capacitors, anode to cathode alignment is typically maintained through the use of adhesive electrolyte as disclosed in the above-referenced patents to MacFarlane, supra. The above-referenced '851 patent describes a flat aluminum electrolytic capacitor wherein the housing of the capacitor has at least two internal alignment members. Those alignment members necessarily add volume to the capacitor while taking away from the total amount of "active" electrode material available, thereby decreasing the energy density of the capacitor. Moreover, the above-referenced '082 patent describes use of inwardly directed registration notches in the capacitor electrode stack periphery that are used during registration of the stack within the interior case chamber which reduce capacity. The '082 patent also provides for cathode layer peripheral edges that extend outward beyond the anode layer peripheral edges through a major portion of the electrode stack periphery that can electrically contact the case. This approach is wasteful of space that could be used by anode layers to increase capacity.

SUMMARY OF THE INVENTION

Accordingly, the present invention is directed to providing efficient usage of the space within the interior case chamber of an electrolytic capacitor particularly adapted for use in IMDs. The capacitor is formed with an electrode stack assembly comprising a plurality of stacked capacitor layers each comprising an anode sub-assembly of at least one anode layer, a cathode layer and separator layers wherein the anode and cathode layers have differing dimensions that avoid electrical short circuits between peripheral edges of adjacent anode and cathode layers due to edge defects but maximize anode electrode surface area.

In a preferred embodiment the electrolytic capacitor is formed of a capacitor case defining an interior case chamber and case chamber periphery, an electrode stack assembly of a plurality of stacked capacitor layers having anode and cathode tabs disposed in the interior case chamber, an electrical connector assembly for providing electrical connection with the anode and cathode tabs through the case, a cover, and electrolyte filling the remaining space within the interior case chamber.

The plurality of capacitor layers and further separator layers are stacked into the electrode stack assembly and disposed within the interior case chamber such that the adjacent anode and cathode layers are electrically isolated from one another. The anode layer peripheral edges of the anode subassemblies of the stacked capacitor layers extend closer to the case side wall than the cathode peripheral edges of the cathode layers of the stack of capacitor layers throughout a major portion of the case chamber periphery. The separator layer peripheral edges extend to the case periphery and space the anode layer peripheral edges therefrom. Any burrs, debris or distortions or deformations or other edge defects along any of the anode layer peripheral edges causing the anode layer edges to effectively extend in the electrode stack height direction causes the anode layer peripheral edges having such tendency to contact an adjacent anode layer. In this way, anode layer surface area is maximized, and short circuiting of the anode layers with the cathode layers is avoided.

A case liner can also be disposed around the electrode stack assembly periphery.

Those of ordinary skill in the art will understand immediately upon referring to the drawings, detailed description of the preferred embodiments and claims hereof that many objects, features and advantages of the capacitors and methods of the present invention will find application in the fields other than the field of IMDs.

BRIEF DESCRIPTION OF THE DRAWINGS

These and other advantages and features of the present invention will be appreciated as the same becomes better understood by reference to the following detailed description of the preferred embodiment of the invention when considered in connection with the accompanying drawings, in which like numbered reference numbers designate like parts throughout the figures thereof, and wherein:

FIGS. 3(a)–3(g) are exploded perspective views of the manner in which the various components of the exemplary ICD IPG of FIGS. 1 and 2, including the electrolytic capacitors of the present invention, are disposed within the housing of the ICD IPG;

FIG. 5(a) is an exploded perspective view of one embodiment of a cold welding apparatus in which anode layers of the electrode stack subassembly of FIG. 4 are cold-welded;

FIG. 5(b) is an unexploded view of the cold welding apparatus of FIG. 5(a);

DETAILED DESCRIPTION OF THE PREFERRED EMBODIMENTS

Figure 1:
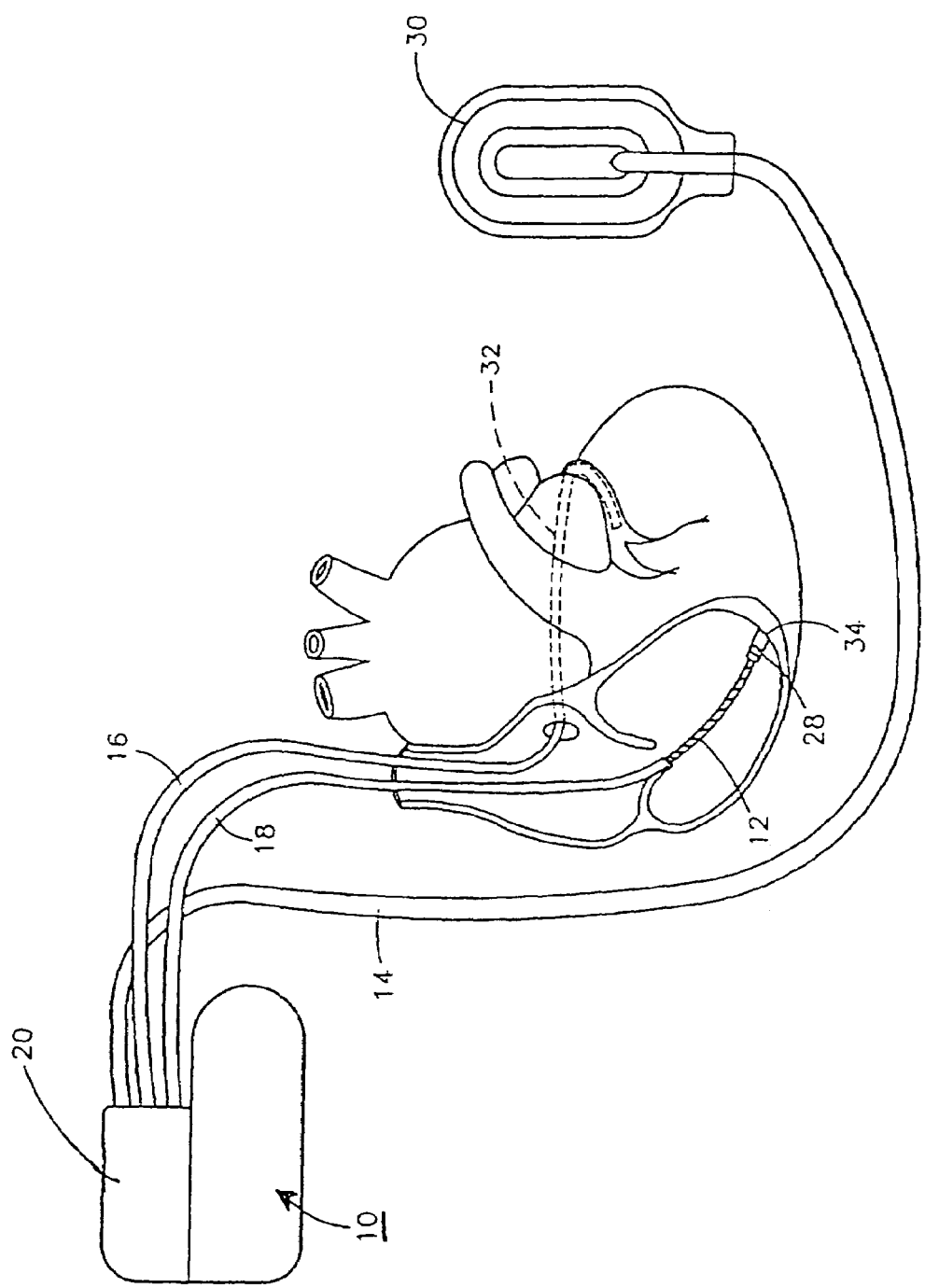
FIG. 1 illustrates the physical components of one exemplary embodiment of an ICD IPG and lead system in which the present invention may be advantageously incorporated.

FIG. 1 illustrates one embodiment of ICD IPG 10 in which the capacitor of the present invention is advantageously incorporated, the associated ICD electrical leads 14, 16 and 18, and their relationship to a human heart 12. The leads are coupled to ICD IPG 10 by means of multi-port connector block 20, which contains separate connector ports for each of the three leads illustrated. Lead 14 is coupled to subcutaneous electrode 30, which is intended to be mounted subcutaneously in the region of the left chest. Lead 16 is a coronary sinus lead employing an elongated coil electrode which is located in the coronary sinus and great vein region of the heart. The location of the electrode is illustrated in broken line format at 32, and extends around the heart from a point within the opening of the coronary sinus to a point in the vicinity of the left atrial appendage.

Lead 18 is provided with elongated electrode coil 28 which is located in the right ventricle of the heart. Lead 18 also includes stimulation electrode 34 which takes the form of a helical coil which is screwed into the myocardial tissue of the right ventricle. Lead 18 may also include one or more additional electrodes for near and far field electrogram sensing.

In the system illustrated, cardiac pacing pulses are delivered between helical electrode 34 and elongated electrode 28. Electrodes 28 and 34 are also employed to sense electrical signals indicative of ventricular contractions. As illustrated, it is anticipated that the right ventricular electrode 28 will serve as the common electrode during sequential and simultaneous pulse multiple electrode defibrillation regimens. For example, during a simultaneous pulse defibrillation regimen, pulses would simultaneously be delivered between electrode 28 and electrode 30 and between electrode 28 and electrode 32. During sequential pulse defibrillation, it is envisioned that pulses would be delivered sequentially between subcutaneous electrode 30 and electrode 28 and between coronary sinus electrode 32 and right ventricular electrode 28. Single pulse, two electrode defibrillation shock regimens may be also provided, typically between electrode 28 and coronary sinus electrode 32. Alternatively, single pulses may be delivered between electrodes 28 and 30. The particular interconnection of the electrodes to an ICD will depend somewhat on which specific single electrode pair defibrillation shock regimen is believed more likely to be employed.

Figure 2:
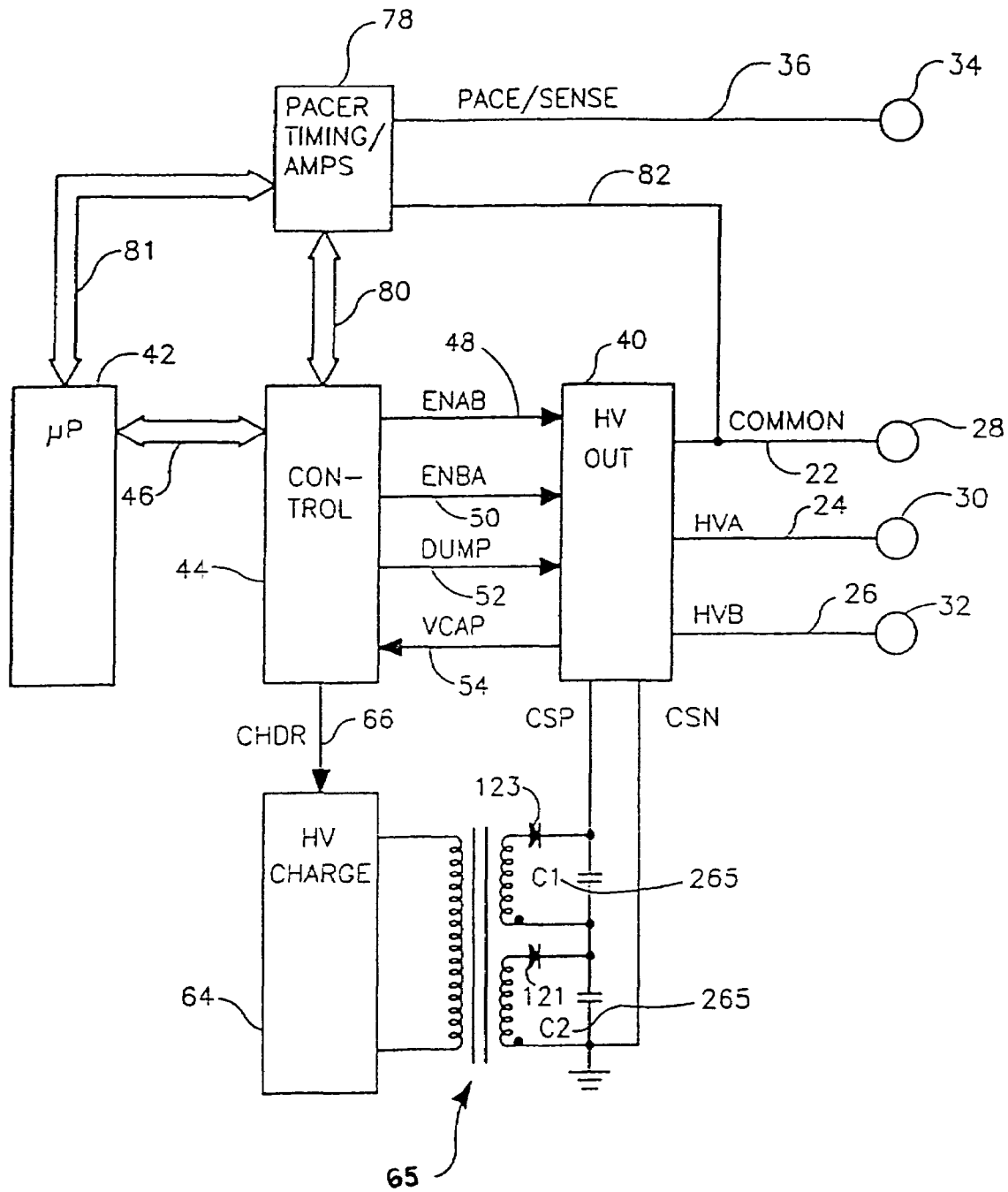
FIG. 2 is a simplified functional block diagram illustrating the interconnection of voltage conversion circuitry with the high voltage capacitors of the present invention with the primary functional components of one type of an ICD IPG.

FIG. 2 is a block diagram illustrating the interconnection of high voltage output circuit 40, high voltage charging circuit 64 and capacitors 265 according to one example of the microcomputer based operating system of the ICD IPG of FIG. 1. As illustrated, the ICD operations are controlled by means of a stored program in microprocessor 42, which performs all necessary computational functions within the ICD. Microprocessor 42 is linked to control circuitry 44 by means of bidirectional data/control bus 46, and thereby controls operation of the output circuitry 40 and the high voltage charging circuitry 64. Pace/sense circuitry 78 awakens microprocessor 42 to perform any necessary mathematical calculations, to perform tachycardia and fibrillation detection procedures and to update the time intervals controlled by the timers in pace/sense circuitry 78 on reprogramming of the ICD operating modes or parameter values or on the occurrence of signals indicative of delivery of cardiac pacing pulses or of the occurrence of cardiac contractions,.

The basic operation and particular structure or components of the exemplary ICD of FIGS. 1 and 2 may correspond to any of the systems known in the art, and the present invention is not dependent upon any particular configuration thereof. The flat aluminum electrolytic capacitor of the present invention may be employed generally in conjunction with the various systems illustrated in the aforementioned '209 patent, or in conjunction with the various systems or components disclosed in the various U.S. patents listed in the above-referenced parent patent application Ser. No. 09/531,352.

Control circuitry 44 provides three signals of primary importance to output circuitry 40. Those signals include the first and second control signals discussed above, labeled here as ENAB, line 48, and ENBA, line 50. Also of importance is DUMP line 52 which initiates discharge of the output capacitors and VCAP line 54 which provides a signal indicative of the voltage stored on the output capacitors C1, C2, to control circuitry 44. Defibrillation electrodes 28, 30 and 32 illustrated in FIG. 1, above, are shown coupled to output circuitry 40 by means of conductors 22, 24 and 26. For ease of understanding, those conductors are also labeled as "COMMON", "HVA" and "HVB". However, other configurations are also possible. For example, subcutaneous electrode 30 may be coupled to HVB conductor 26, to allow for a single pulse regimen to be delivered between electrodes 28 and 30. During a logic signal on ENAB, line 48, a cardioversion/defibrlllation shock is delivered between electrode 30 and electrode 28. During a logic signal on ENBA, line 50, a cardioversion/defibrillation shock is delivered between electrode 32 and electrode 28.

The output circuitry includes a capacitor bank, including capacitors C1 and C2 and diodes 121 and 123, used for delivering defibrillation shocks to the electrodes. Alternatively, the capacitor bank may include a further set of capacitors as depicted in the above referenced '758 application. In FIG. 2, capacitors 265 are illustrated in conjunction with high voltage charging circuitry 64, controlled by the control/timing circuitry 44 by means of CHDR line 66. As illustrated, capacitors 265 are charged by means of a high frequency, high voltage transformer 65. Proper charging polarities are maintained by means of the diodes 121 and 123. VCAP line 54 provides a signal indicative of the voltage on the capacitor bank, and allows for control of the high voltage charging circuitry and for termination of the charging function when the measured voltage equals the programmed charging level.

Pace/sense circuitry 78 includes an R-wave sense amplifier and a pulse generator for generating cardiac pacing pulses, which may also correspond to any known cardiac pacemaker output circuitry and includes timing circuitry for defining ventricular pacing intervals, refractory intervals and blanking intervals, under control of microprocessor 42 via control/data bus 80.

Control signals triggering generation of cardiac pacing pulses by pace/sense circuitry 78 and signals indicative of the occurrence of R-waves, from pace/sense circuitry 78 are communicated to control circuitry 44 by means of a bi-directional data bus 81. Pace/sense circuitry 78 is coupled to helical electrode 34 illustrated in FIG. 1 by means of a conductor 36. Pace/sense circuitry 78 is also coupled to ventricular electrode 28, illustrated in FIG. 1, by means of a conductor 82, allowing for bipolar sensing of R-waves between electrodes 34 and 28 and for delivery of bipolar pacing pulses between electrodes 34 and 28, as discussed above.

Figure 3A:
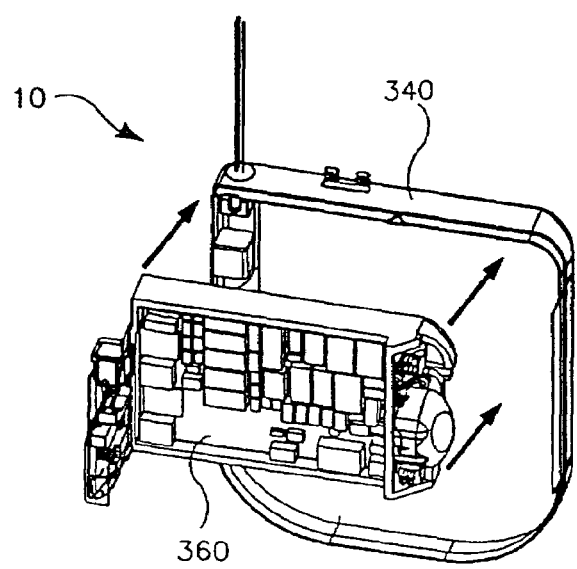
Figure 3B:
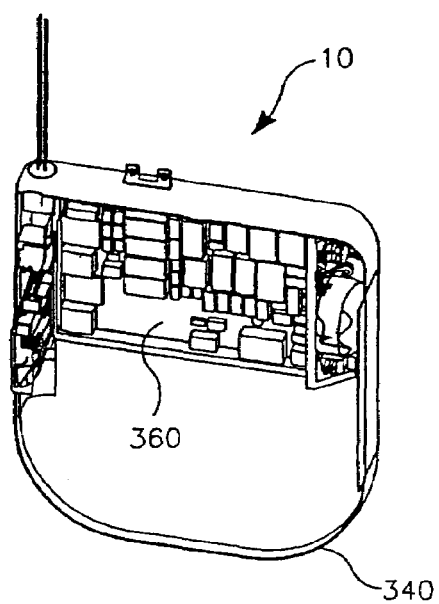

FIGS. 3(a) through 3(g) show perspective views of various components of ICD IPG 10, including one embodiment of the capacitor of the present invention, as those components are placed successively within the housing of ICD IPG 10. In FIG. 3(a), electronics module 360 is placed in right-hand shield 340 of ICD IPG 10. FIG. 3(b) shows ICD IPG 10 once electronics module 360 has been seated in tight-hand shield 340.

FIG. 3(c) shows a pair of capacitors 265 formed as described herein prior to being placed within right-hand shield 340, the capacitors 265 being connected electrically in series by interconnections in electronics module 340. FIG. 3(d) shows ICD IPG 10 once the pair of capacitors 265 has been placed within right-hand shield 340.

Figure 3F:
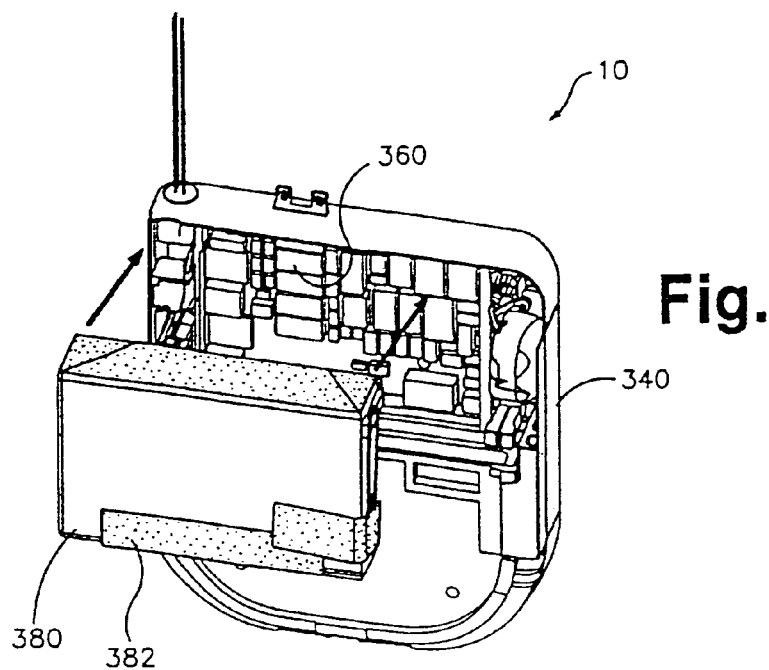

FIG. 3(e) shows insulator cup 370 prior to its placing atop capacitors 265 in right-hand shield 340. FIG. 3(f) shows electrochemical cell or battery 380 having insulator 382 disposed around battery 380 prior to placing it in shield 340. Battery 380 provides the electrical energy required to charge and re-charge capacitors 265, and also powers electronics module 360. Battery 380 may take any of the forms employed in the prior art to provide cardioversion/defibrillation energy, some of which are identified in parent patent application Ser. No. 09/531,352.

Figure 3G:
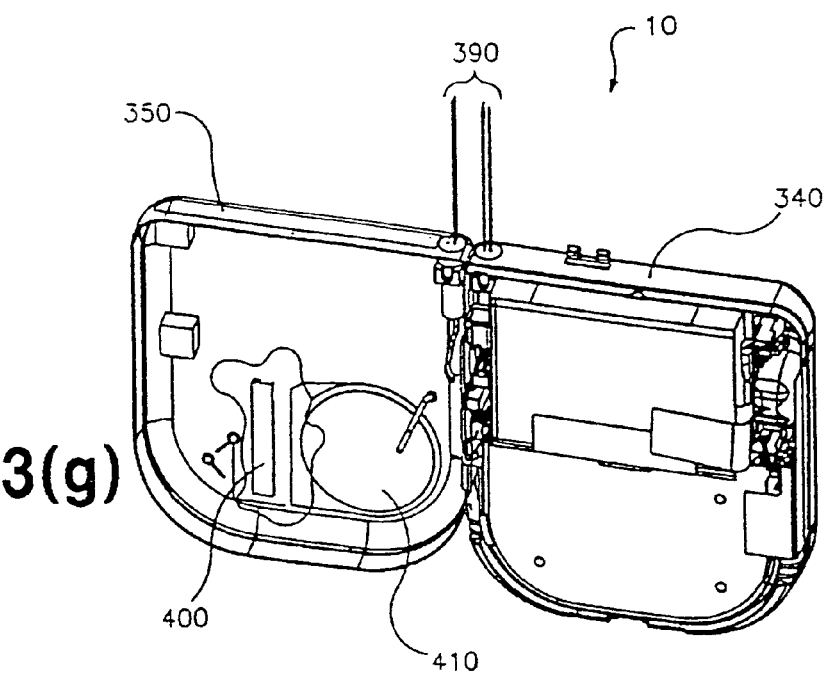

FIG. 3(g) shows ICD IPG 10 having left-hand shield 350 connected to right-hand shield 340 and feedthrough 390 projecting upwardly from both shield halves. Activity sensor 400 and patient alert apparatus 410 are shown disposed on the side lower portion of left-hand shield 350. Left-hand shield 350 and right-hand shield 340 are subsequently closed and hermetically sealed (not shown in the figures).

Figure 4:
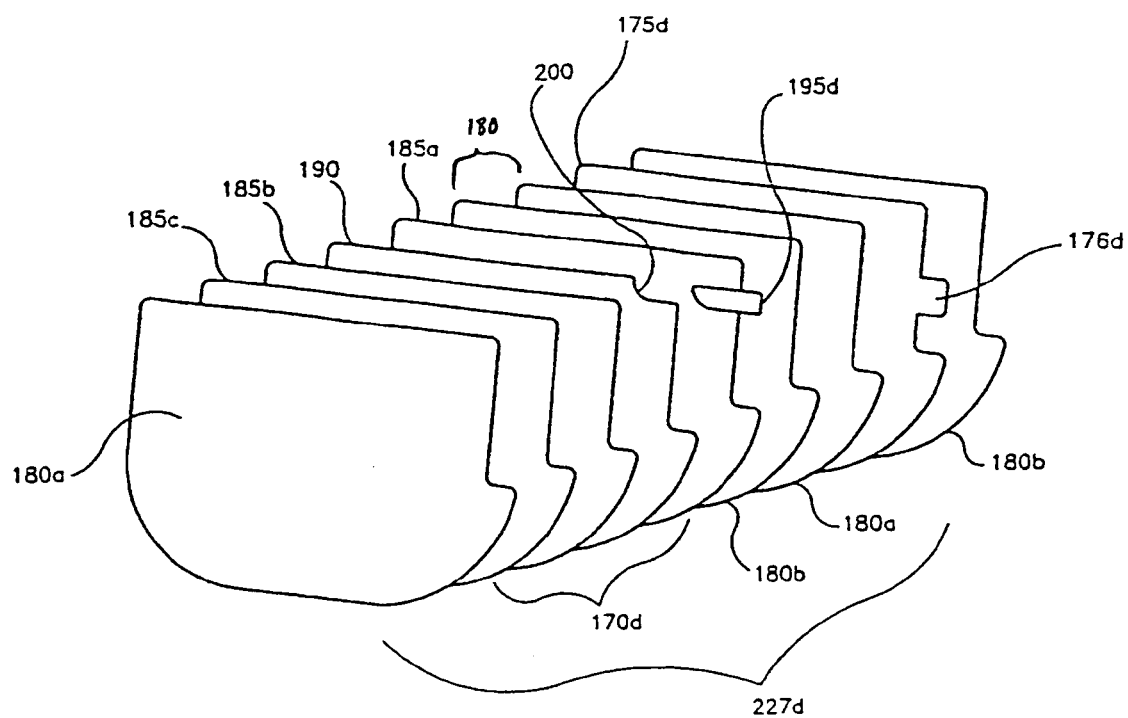
FIG. 4 is an exploded view of one embodiment of a single anode/cathode layer or electrode stack sub-assembly of an electrolytic capacitor incorporating the present invention.

FIG. 4 shows an exploded view of one embodiment of a capacitor layer or single anode/cathode sub-assembly 227 of capacitor 265. The capacitor design described herein employs a stacked configuration of a plurality of capacitor layers or single anode/cathode sub-assemblies 227 as further described below with respect to FIG. 6. Each anode/cathode sub-assembly 227 comprises alternating substantially rectangular-shaped anode layers 185 and cathode layers 175, with a substantially rectangular-shaped separator layer 180 being interposed therebetween. The shapes of anode layers 185, cathode layers 175 and separator layers 180 are primarily a matter of design choice, and are dictated largely by the shape or configuration of case 90 within which those layers are ultimately disposed. Anode layers 185, cathode layers 175 and separator layers 180 may assume any arbitrary shape to optimize packaging efficiency.

Anode sub-assembly 170d most preferably comprises a plurality of non-notched anode layers 185a, 185b, 185c, notched anode layer 190 including anode tab notch 200, and anode tab 195 coupled to anode layer 185a. It will be understood that anode sub-assembly 170d shown in FIG. 4 is but one possible embodiment of an anode sub-assembly 170. Cathode layer 175d most preferably is formed of a single sheet and has cathode tab 176 formed integral thereto and projecting from the periphery thereof.

In one preferred embodiment of the sub-assembly 227 as depicted in the figures, two individual separator layer sheets 180a and 180b form the separator layer 180 that is disposed between each anode sub-assembly 170 and cathode layer 175. Further single separator layer sheets 180a and 180b are disposed against the outer surfaces of the anode layer 185c and the cathode layer 175d. When the sub-assemblies are stacked, the outermost single separator layer sheets 180a and 180b bear against adjacent outermost single separator layer sheets 180b and 180a, respectively, of adjacent capacitor layers so that two sheet separator layers 180 separate all adjacent cathode and anode layers of an electrode stack assembly 225.

It will be understood by those skilled in the art that the precise number of sub-assemblies 227 selected for use in a electrode stack assembly 225 will depend upon the energy density, volume, voltage, current, energy output and other requirements placed upon capacitor 265. Similarly, it will be understood by those skilled in the art that the precise number of notched and un-notched anode layers 185, anode tabs 195, anode sub-assemblies 170, cathode layers 175 and separator layers 180 selected for use in a given embodiment of anode/cathode sub-assembly 227 will depend upon the energy density, volume, voltage, current, energy output and other requirements placed upon capacitor 265. It will now become apparent that a virtually unlimited number of combinations and permutations respecting the number of anode/cathode sub-assemblies 227, and the number of un-notched and notched anode layers 185 forming anode sub-assembly 170, anode sub-assemblies 170, anode tabs 195, cathode layers 175 and separator layers 180 disposed within each anode/cathode sub-assembly 227, may be selected according to the particular requirements of capacitor 265. Anode layers 185, cathode layers 175 and separator layers 180 are most preferably formed of materials typically used in high quality aluminum electrolytic capacitors, Anode layers 185 and 190 are formed of anode foil that is most preferably through-etched, has a high specific capacitance (at least about 0.3, at least about 0.5 or most preferably at least about 0.8 microfarads/cm$^2$), has a dielectric withstand parameter of at least 425 Volts DC, a thickness ranging between about 50 and about 200 micrometers, more preferably between about 75 and 150 micrometers, more preferably yet between about 90 and about 125 micrometers, and most preferably being about 100 micrometers thick, and a cleanliness of about 1.0 mg/m$^2$ respecting projected area maximum chloride contamination. The anode foil preferably has a rated surge voltage of 390 Volts, an initial purity of about 99.99% aluminum, a final thickness of about 104 micrometers, plus or minus about five micrometers, and a specific capacitance of about 0.8 microfarads per square centimeter. Suitable anode foils are commercially available on a widespread basis.

Individual anode layers 185 are typically somewhat stiff and formed of high-purity aluminum processed by etching to achieve high capacitance per unit area. Thin anode foils are preferred, especially if they substantially maintain or increase specific capacitance while reducing the thickness of the electrode stack assembly 225, or maintain the thickness of electrode stack assembly 225 while increasing overall capacitance. For example, it is contemplated that individual anode layers 185 have a thickness of about 10 micrometers, about 20 micrometers, about 30 micrometers, about 40 micrometers, about 50 micrometers, about 60 micrometers, about 70 micrometers, about 80 micrometers, about 90 micrometers, about 100 micrometers, about 110 micrometers, about 120 micrometers, about 130 micrometers, about 140 micrometers and about 150 micrometers.

Cathode layers 175 are preferably high purity and are comparatively flexible. Cathode layers 175 are most preferably formed from cathode foil having high surface area (i.e., highly etched cathode foil), high specific capacitance (preferably at least 200 microfarads/cm², and at least 250 microfarads/cm² when fresh), a thickness of about 30 micrometers, a cleanliness of about 1.0 mg/m² respecting projected area maximum chloride contamination, and a purity which may be less than corresponding to the starting foil material from which anode foil is made. The cathode foil preferably has an initial purity of at least 99% aluminum, and more preferably yet of about 99.4% aluminum, a final thickness of about 30 micrometers, and an initial specific capacitance of about 250 microfarads per square centimeter. In other embodiments, cathode foil has a specific capacitance ranging between about 100 and about 500 microfarads/cm², about 200 and about 400 microfarads/cm², or about 250 and about 350 microfarads/cm², a thickness ranging between about 10 and about 150 micrometers, about 15 and about 100 micrometers, about 20 and about 50 micrometers, or about 25 and about 40 micrometers.

It is generally preferred that the specific capacitance of the cathode foil be as high as possible, and that cathode layer 175 be as thin as possible. For example, it is contemplated that individual cathode layers 175 have specific capacitances of about 100 microfarads/cm², about 200 microfarads/cm², about 300 microfarads/cm², about 400 microfarads/cm², about 500 microfarads/cm², about 600 microfarads/cm², about 700 microfarads/cm², about 800 microfarads/cm², about 900 microfarads/cm², or about 1,000 microfarads/cm². Suitable cathode foils are commercially available on a widespread basis. In still other embodiments, cathode foil is formed of materials or metals in addition to aluminum, aluminum alloys and "pure" aluminum.

Separator layer sheets 180a and 180b outer separator layers 165a and 165b are most preferably made from a roll or sheet of separator material. Separator layers 180 are preferably cut slightly larger than anode sub-assemblies 170 and cathode layers 175 to accommodate misalignment during the stacking of layers, to prevent subsequent shorting between anode and cathode layers, and to otherwise ensure that a physical barrier is disposed between the anodes and the cathodes of the finished capacitor. In accordance with the present invention, the anode sub-assemblies 170 are also cut larger than the cathode layers 175.

It is preferred that separator layer sheets 180a and 180b and exterior separator layers 165a and 165b (shown in FIG. 9) be formed of a material that: (a) is chemically inert; (b) is chemically compatible with the selected electrolyte; (c) may be impregnated with the electrolyte to produce a low resistance path between adjoining anode and cathode layers, and (d) physically separates adjoining anode and cathode layers. In one preferred embodiment, separator material is a pure cellulose, very low halide or chloride content Kraft paper having a thickness of about 0.0005 inches (0.0013 mm), a density of about 1.06 grams/cm³, a dielectric strength of 1,400 Volts AC per 0.001 inch (0.025 mm) thickness, and a low number of conducting paths (about 0.4/ft² or less). Separator layer sheets 180a and 180b and outer separator layers 165a and 165b may also be formed of materials other than Kraft paper, such as Manila paper, porous polymeric materials or fabric gauze materials. For example, porous polymeric materials may be disposed between anode and cathode layers like those disclosed in U.S. Pat. Nos. 3,555,369 and 3,883,784 in some embodiments of the capacitor layers In such capacitor stacks formed of a plurality of capacitor layers, a liquid electrolyte saturates or wets separator layers 180 and is disposed within case 90. It is to be understood, however, that various embodiments include within their scope a solid or adhesive electrolyte such as those disclosed in U.S. Pat. Nos. 5,628,801; 5,584,890; 4,942,501, 5,146, 391 and 5,153,820. Note that an appropriate inter-electrode adhesives/electrolyte layer may be employed in place of paper, gauze or porous polymeric materials to form separator layer 180.

Continuing to refer to FIG. 4, a first preferred step in assembling a flat aluminum electrolytic capacitor is to cut anode layers 185 and 190, anode tabs 195, cathode layers 175 and separator layers 180. Those components are most preferably cut to shape using dies having low wall-to-wall clearance, where inter-wall spacing between the substantially vertically-oriented corresponding walls of the punch and die is most preferably on the order of about 6 millionths of an inch per side. Larger or smaller inter-wall spacings between the substantially vertically-oriented corresponding walls of the punch and cavity, such as about 2, about 4, about 5, about 7, about 8, about 10 and about 12 millionths of an inch may also be employed but are less preferred.

Such low clearance results in smooth, burr free edges being formed along the peripheries of anode layers 185 and 190, anode tabs 195, cathode layers 175 and separator layers 180. Smooth, burr free edges on the walls of the dies have been discovered to be critical respecting reliable performance of a capacitor. The presence of burrs along the peripheries of anode layers 185 and 190, anode tabs 195, cathode layers 175 and separator layers 180 may result in electrical short circuit and failure of the capacitor. The means by which anode foil, cathode foil and separator materials are cut or formed may have a significant impact on the lack or presence of burrs and other cutting debris disposed about the peripheries of the formed or cut members. The use of low clearance dies produces an edge superior to the edge produced by other cutting methods, such as steel rule dies. The shape, flexibility and speed of a low clearance die have been discovered to be superior to those achieved by laser or blade cutting. Other methods of cutting or forming anode layers 185 and 190, anode tabs 195, cathode layers 175 and separator layers 180 include, but are not limited to, steel rule die cutting, laser cutting, water jet cutting and blade cutting.

In spite of these precautions taken in carefully and cleanly cutting the anode and cathode peripheral edges, some amount of burrs, cutting debris, deformations of the peripheral edges (collectively referred to as edge defects) of the anode layers during cutting or subsequent handling and welding of anode layers into anode sub-assemblies can still occur. The present invention provides a configuration and assembly method that prevents such anode layer edge defects from short circuiting with adjacent cathode layers.

The preferred low clearance of the die apparatus is especially important for cutting thin ductile materials such as the cathode foil. In addition to improving reliability, burr and debris reduction permits reductions in the thickness of separator layer 180, thereby improving energy density of the capacitor. Angle cutting, where the face of the punch is not held parallel to the opposing floor of the die during the cutting step, is another less preferred method of cutting or forming anode layers 185 and 190, anode tabs 195, cathode layers 175 and separator layers 180.

In a preferred method, foil or separator materials are drawn between the punch and cavity portions of a die having appropriate clearances on a roll. An air or hydraulically actuated press is then most preferably employed to actuate the punch or cavity portion of the die. The punch portion of the die is most preferably formed of hardened tool steel, or has other suitable wear resistant materials or coatings disposed on the cutting surfaces thereof. When the cavity of the die is aligned vertically, the punch portion of the die may travel either upwards or downwards towards the die cavity during a cutting cycle. In the former case, components are cut and drop downwardly into a container for use in subsequent assembly operations. In the latter case, components are cut and may be presented directly to automated assembly equipment, such as robots equipped with vacuum or other pick-up tooling, for subsequent processing. Low clearance dies of the type described herein may be supplied by Top Tool, Inc. of Minneapolis, Minn.

Anode sub-assembly 170 most preferably includes one notched anode layer 190, which facilitates appropriate placing and positioning of anode tab 195 within anode sub-assembly 170. More than one notched anode layer 190 may also be included in anode sub-assembly 170. It is preferred that the remaining anode layers of anode sub-assembly 170 be non-notched anode layers 185. Anode tab 195 is most preferably formed of aluminum strip material. In one preferred embodiment, the aluminum strip material has a purity of about 99.99% aluminum and a lesser degree of anodization than the anode foil. When anode tab 195 is formed of a non-anodized material, cold welding of anode tab 195 to non-notched anode layers 185 may be accomplished with less force and deflection, more about which we say below. It is preferred that the thickness of anode tab 195 be about equal to that of notched anode layer 190. If more than one notched anode layer 190 is employed in anode sub-assembly 170, a thicker anode tab 195 may be employed.

Figure 5C:
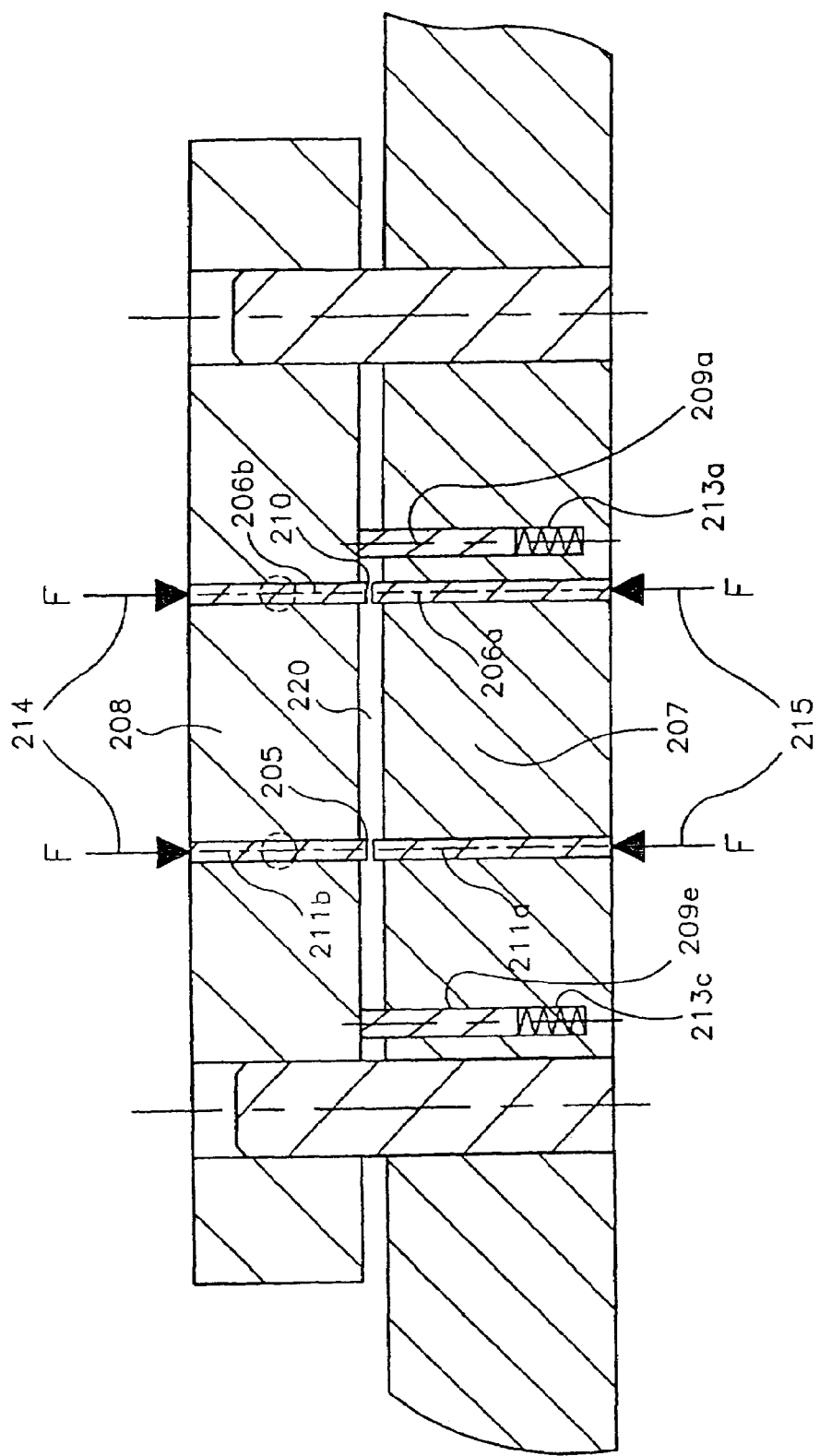
FIG. 5(c) is a cross-sectional view of the cold welding apparatus of FIGS. 5(a) and 5(b) in which anode layers of the electrode sub-assembly of FIG. 4 are cold-welded therein.

Referring now to FIGS. 5(a) through 5(c), two non-notched anode layers 185a and 185b are placed on cold welding fixture base layer 207 of cold welding apparatus 202. The various structural members of cold welding apparatus 202 are most preferably formed of precision machined stainless steel or a high strength aluminum alloy. Layers 185a and 185b are next aligned and positioned appropriately on cold welding fixture base layer 207 using spring loaded alignment pins 209a through 209e. Pins 209a through 209e retract upon top layer 208 being pressed downwardly upon layers 185a and 185b disposed within cold welding cavity 220. See also FIG. 5(c), where a cross-sectional view of cold welding apparatus 202 is shown.

Anode layer 190 is similarly disposed within cavity 220, followed by placing anode tab 195 within anode tab notch 200 in notched anode layer 190. Anode tab 195 is most preferably positioned along the periphery of notched anode layer 190 with the aid of additional spring loaded alignment pins 209f and 209g disposed along the periphery of anode tab 195. Non-notched anode layer 185c is then placed atop anode layer 190. Stacked anode sub-assembly 170 is then clamped between top plate 208 and base plate 207. Disposed within base plate 207 are anode layer cold welding pins 206a and anode tab cold welding pin 211a. Disposed within top plate 208 are anode layer cold welding pin 206b and anode tab cold welding pin 211b. Base plate 207 and top plate 208 are aligned such that the axes of cold welding pins 206a and 206b coincide with and are aligned respecting corresponding cold welding pins 211a and 211b.

Upper actuation apparatus 214 of cold welding apparatus 202 displaces cold welding pins 206b and 211b downwardly. Lower actuation apparatus 215 displaces cold welding pins 206a and 211a upwardly. In one embodiment of upper actuation apparatus 214 and lower actuation apparatus 215, pneumatic cylinders are employed to move pins 206a, 206b, 211a and 211b. In another embodiment of apparatus 214 and apparatus 215, a pair of rolling wheels is provided that move simultaneously and perpendicularly to the axes of pins 206a, 206b, 211a, and 211b. Still other embodiments of apparatus 214 and apparatus 215 may employ hydraulic actuators, cantilever beams, dead weights, springs, servomotors electromechanical solenoids, and the like for moving pins 206a, 206b, 211a and 211b. Control of actuation apparatus 214 and apparatus 215 respecting pin displacement force magnitude and timing may be accomplished using any one or combination of constant load, constant displacement, solenoid controller, direct or indirect means.

Following clamping with top plate 208, cold welding pins 206a, 206b, 211a and 211b are actuated. Cold welds 205 and 210 in anode sub-assembly 170 are formed by compression forces generated when cold weld pins 206a, 206b, 211a and 211b are compressed against anode sub-assembly 170. See FIG. 6(a), where the preferred regions in which cold welds 205 and 210 are formed are shown. Cold welds 205 and 210 may be described as not only cold welds, but forged welds. This is because the interfacial boundaries between anode layers 185 are deformed in the region of welds 205 and 210, thereby disrupting oxide layers and bringing base metals into direct contact with one another where metallic bonding occurs. Metallic bonding increases the strength of the welds.

In one embodiment of the method, a plurality of pneumatic cylinders function simultaneously in upper actuation apparatus 214 and lower actuation apparatus 215 to drive pins 206a, 206b, 211a and 211b against anode sub-assembly 170. Anode layer cold weld 205 and anode tab cold weld 210 are most preferably formed under direct constant load conditions, where pneumatic cylinders are pressurized to a predetermined fixed pressure. Anode layer cold weld 205 and anode tab cold weld 210 may also be formed under indirect constant displacement conditions, where pneumatic cylinders are pressurized until a displacement sensor placed across cold welding pins 206a, 206b, 211a or 211b generates a signal having a predetermined value, whereupon those pins are disengaged from anode/cathode sub-assembly 227.

In another embodiment of the method, a cantilever beam mechanism is incorporated into upper actuation apparatus 214 and lower actuation apparatus 215. Anode layer cold weld 205 and anode tab cold weld 210 are formed under direct constant displacement conditions, where cantilever beams are actuated and cause upper and lower members 208 and 207 to engage anode/cathode sub-assembly 227 until a hard stop point is reached. An indirect load controlled system may also be employed in apparatus 214 and apparatus 215, where cantilever or other means include a load measuring sensor for controlling the stop point of the cantilever beam, for example, when a predetermined load is measured by the sensor.

The cross-sectional shape of cold weld pins 206a, 206b, 211a and 211b may be square, circular, oval or any other suitable shape. The shape of the ends of cold weld pins 206a, 206b, 211a and 211b may be flat, rounded, domed or any other suitable shape appropriate for selectively controlling the properties of the cold welds produced therein. Likewise, more or fewer than four cold weld pins may be employed. The ends of cold weld pins 206a, 206b, 211a and 211b are most preferably rounded or domed and circular in cross-section. Cold weld pins 206a, 206b, 211a and 211b preferably have a diameter of about 0.060 inches (0.174 mm) and further have a beveled or radiused end. Cold weld pins 206a, 206b, 211a and 211b are preferably made from a high strength material that does not readily deform under the pressures obtained during welding, such as stainless steel, titanium, tool steel or HSLA steel. The ends or side walls of cold welding pins 206a, 206b, 211a and 211b may be coated, clad or otherwise modified to increase wear resistance, deformation resistance or other desirable tribilogical attributes of the pins.

The primary function of cold welds 205 and 210 is to provide electrical interconnections between layers 185a, 185b, 185c and 190 and anode tab 195, while mrinimizing the overall thickness of anode sub-assembly 170 in the regions of welds 205 and 210. Typical prior art commercial cylindrical capacitors exhibit a significant increase in the thickness of the anode layer in the regions of the cold welds. This increase in thickness is typically on the order of about two times the thickness of the tab, or about 0.008 inch (0.020 mm). In the case of cylindrical capacitors where only one or two non-coincident tab connections are present, the overall effect on anode layer thickness may be minimal. In a stacked layer design having many more interconnections and welds, however, increases in weld zone thickness have been found to significantly increase the overall thickness of the anode layer and the capacitor stack as a whole.

In one cold welding method and corresponding apparatus, no or an inappreciable net increase in anode sub-assembly 170 thickness results when cold weld geometries and formation processes are appropriately optimized. Several embodiments of anode-assembly 170 have been found to have no more than about a 20% increase in layer thickness due to the presence of cold welds, as compared to about a 200% increase in thickness resulting from cold welds found in some commercial cylindrical capacitors. Two, three, four, five, six or more anode layers 185 and 190 may be cold-welded to form anode sub-assembly 170 as described herein.

Figure 6A:
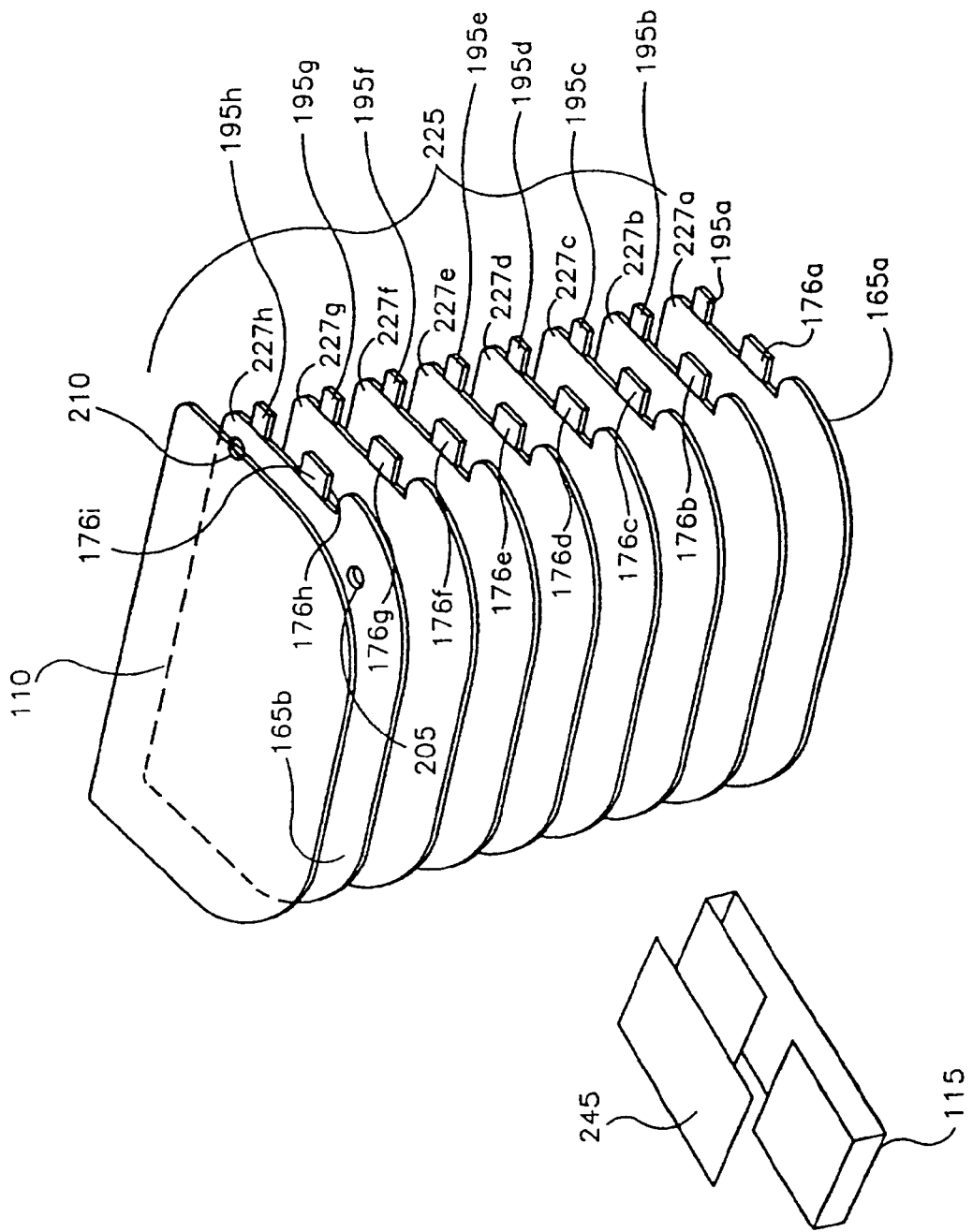
FIG. 6(a) is an exploded top perspective view of one embodiment of a plurality of capacitor layers of an electrode stack assembly of an electrolytic capacitor incorporating the present invention.
Figure 6B:
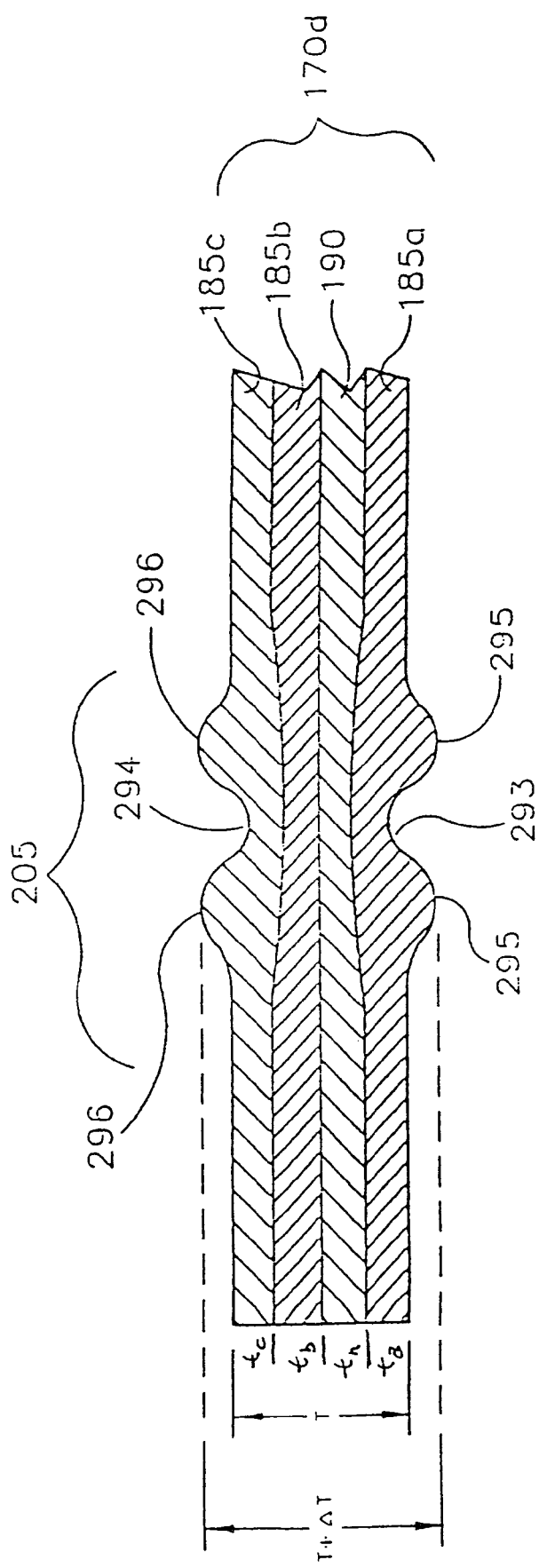
FIG. 6(b) is a cross-sectional view of a portion of one embodiment of a cold-welded anode assembly used in the electrolytic capacitor.

FIG. 6(b) shows a cross-sectional view of a portion of one embodiment of a cold-welded anode assembly formed in accordance with the preferred cold welding method. Anode layers 185a, 190, 185b and 185c having anode layer thicknesses $t_a$, $t_N$, $t_b$ and $t_c$, respectively, are cold-welded together at weld 205 through the compressive action of pins 206a and 206b mounted in bottom plate 207 and top plate 208, respectively. Pins 206a and 206b form central depressions 293 and 294, respectively, in anode sub-assembly 170d, and further result in the formation of rims 295 and 296, respectively. Rims 295 and 296 project downwardly and upwardly, respectively, from the surrounding surfaces of anode sub-assembly 170d, thereby increasing the overall thickness T of anode sub-assembly 170d by $\Delta T$ (T measured in respect of the non-cold-welded surrounding regions or portions of anode sub-assembly 170d).

Figure 6C:
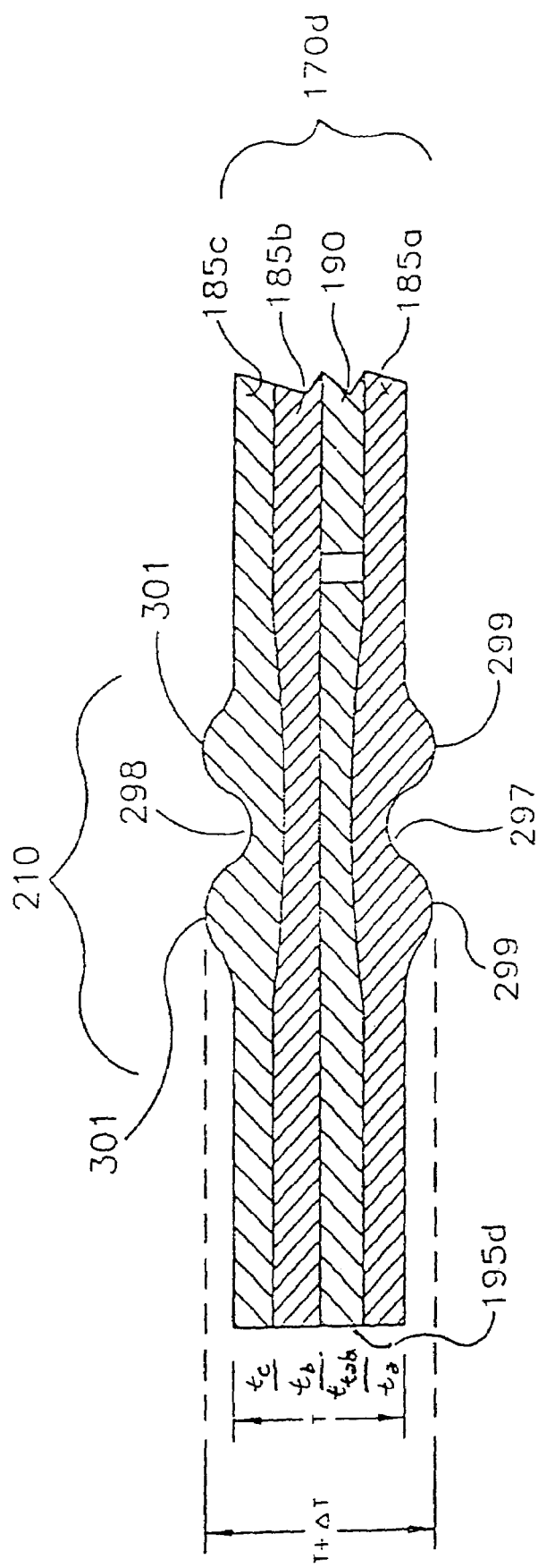
FIG. 6(c) is a cross-sectional view of another portion of one embodiment of a cold-welded anode assembly used in the electrolytic capacitor.

FIG. 6(c) shows a cross-sectional view of another portion of one embodiment of a cold-welded anode assembly wherein anode layers 185a, 185b and 185c and anode tab 195, having anode layer/tab thicknesses $t_a$, $t_b$, $t_c$ and $t_{tab}$, respectively, are cold-welded together at weld 210 through the compressive action of pins 211a and 211b mounted in bottom plate 207 and top plate 208, respectively. Pins 211a and 211b form central depressions 297 and 298, respectively, in anode sub-assembly 170d, and further result in the formation of rims 299 and 301, respectively. Rims 299 and 301 project downwardly and upwardly, respectively, from the surface of anode sub-assembly 170d, thereby increasing overall thickness T of anode sub-assembly 170d by $\Delta T$ (T measured in respect of the non-cold-welded surrounding regions or portions of anode sub-assembly 170d).

The overall thickness T of anode sub-assembly 170d is therefore defined by the equation:

$$T = nt$$

The maximum overall thickness $T+\Delta T$ of anode sub-assembly 170d in the region of cold welds 205 or 210 is then defined by the equation:

$$T+\Delta T = nt + \Delta T$$

where $T_{as}$ is the overall thickness of anode sub-assembly 170d in non-cold-welded regions, n is the number of anode layers 185 and/or 190 in anode sub-assembly 170d, and t is the thickness of individual anode layers 185 and/or 190 or anode tab 195 where the thicknesses $t_n$, $t_a$, $t_b$, $t_c$ and $t_{tab}$, are assumed to be the same.

It is highly desirable to form anode sub-assembly such that the ratio $\Delta T/T$ is less than or equal to 0.05, 0.1, 0.15, 0.20, 0.25, 0.30, 0.35, 0.40, 0.45 or 0.50. The lower the value of the ratio $\Delta T/T$, the greater the volumetric efficiency of capacitor 265. Additionally, the overall thickness of capacitor 265 may be reduced when the value of the ratio $\Delta T/T$ is made smaller.

Referring now to FIG. 6(a), the overall thickness of electrode stack assembly 225 may be reduced further by staggering or offsetting horizontally the respective vertical locations of tabs 195a through 195h (and corresponding cold welds 210). In this embodiment, tabs 195a 195b, for example, are not aligned vertically in respect of one another. Such staggering or offsetting of tabs 195 permits the increases in thickness $\Delta T$ corresponding to each of anode subassemblies 170a through 170h to be spread out horizontally over the perimeter or other portion of electrode stack assembly 225 such that increases in thickness $\Delta T$ do not accumulate or add constructively, thereby decreasing the overall thickness of electrode stack assembly 225. Cold welds 205 may similarly be staggered or offset horizontally respecting one another and cold weld 210 to achieve a reduction in overall thickness of electrode stack assembly 225.

In another preferred embodiment, the anode sub-assembly 170 of each capacitor layer or electrode sub-assembly comprises a plurality of three, four, five or more anode sheets or layers 185 and 190, each sub-assembly most preferably having at least one anode layer having a corresponding anode tab 195 attached thereto or forming a portion thereof, the layers being cold welded together to form anode sub-assembly 170. For example, an anode sub-assembly 170 may comprise six anode layers 185 constructed by cold-welding two separate triple anode layers 185 that were previously and separately cold-welded or otherwise joined together. Alternatively, anode sub-assembly 170 layer may comprise seven anode, layers constructed by cold-welding together one triple anode layer 185 and one quadruple anode layer 185 that were previously and separately cold-welded or otherwise joined together. In another preferred embodiment, multiple notched anode layers 190 may employed in anode sub-assembly 170, thereby permitting the use of a thicker anode tab material.

The geometry of base plate 207 and top plate 208 in the regions surrounding cold welding pins 206a, 206b, 211a and 211b has been discovered to affect the properties of cold welds 205 and 210. In a preferred method, the mating surfaces of plates 207 and 208 surfaces have no radiused break formed in the perimeters of the pin holes. The presence of radiused breaks or chamfers in those regions may cause undesired deformation of cold welds 205 and 210 therein. Such deformation may result in an increase in the thickness of anode sub-assembly 170, which may translate directly into an increase in the thickness of capacitor 265. Note further that the increase in thickness so resulting is a multiple of the number of anode sub-assemblies 170 present in electrode stack assembly 225. Alternatively, radiused breaks or chamfers may be employed in the region of the pin holes in base plate 207 and top plate 208, but appropriate capacitor design accommodations are most preferably made, such as staggering the positions of adjoining stacked cold welds.

Once cold welding pins 206*a*, 206*b*, 211*a* and 211*b* have been actuated against anode sub-assembly 170, top plate 208 is removed and cold-welded anode sub-assembly 170 is provided for further stacking of anode/cathode sub-assembly 227. As illustrated in FIGS. 4, and 6(*a*), this illustrated embodiment of electrode stack assembly 225 most preferably comprises a plurality of cold-welded anode sub-assemblies 175*a* through 175*h*, a plurality of cathode layers 175*a* through 175*i*, a plurality of separator layers 180*a* and 180*b*, outer separator layers 165*a* and 165*b*, outer wrap 115 and wrapping tape 245.

Outer wrap 115 is most preferably die cut from separator material described supra, but may be formed from a wide range of other suitable materials such as polymeric materials, aluminum, suitable heat shrink materials, suitable rubberized materials and synthetic equivalents or derivatives thereof, and the like. Wrapping tape 245 is most preferably cut from a polypropylene-backed acrylic adhesive tape, but may also be replaced by a staple, an ultrasonic paper joint or weld, suitable adhesives other than acrylic adhesive, suitable tape other than polypropylene-backed tape, a hook and corresponding clasp and so on.

Outer wrap 115 and wrapping tape 245 together comprise an electrode stack assembly wrap which has been discovered to help prevent undesired movement or shifting of electrode stack assembly 225 during subsequent processing. It will now become apparent to one skilled in the art that many means other than those disclosed explicitly herein exist for immobilizing and securing electrode stack assembly 225 during subsequent processing which accomplish substantially the same function as the electrode stack assembly wrap comprising outer wrap 115 and wrapping tape 245. Alternative means for immobilizing and securing electrode stack assembly 225 other than those described hereinabove exist. Such alternative means include, but are not limited to, robotic or other mechanical clamping and securing means not necessarily forming a portion of electrode stack assembly 225, adhesive electrolytes for forming separator layers 180, and so on.

The stacking process by which electrode stack assembly 225 is most preferably made begins by placing outer wrap 115 into a stacking fixture followed by placing outer paper or separator layer 165*a* thereon. Next, cathode layer 175*a* is placed atop separator layer 165*a*, followed by separator layers 180*a* and 180*b* being disposed thereon. Cold-welded anode sub-assembly 170*a* is then placed atop separator layer 180*b*, followed by placing separator layers 180*a* and 180*b* thereon, and so on. The placing of alternating cathode layers 175 and anode sub-assemblies 170 with separator layers 180*a* and 180*b* interposed therebetween continues in the stacking fixture until final cathode layer 175*h* has been placed thereon.

In the embodiment of electrode stack assembly 225 shown in FIG. 6(*a*), eight anode sub-assemblies (anode sub-assemblies 170*a* through 170*h*) and nine cathode layers (cathode layers 175*a* through 175*i*) are illustrated. The voltage developed across each combined anode sub-assembly/separator layer/cathode layer assembly disposed within electrode stack assembly 225 most preferably ranges between about 360 and about 390 Volts DC. As described below, the various anode sub-assemblies of electrode stack assembly 225 are typically connected in parallel electrically, as are the various cathode layers of electrode stack assembly 225.

Consistent with the discussion hereinabove concerning FIG. 4, it will now be understood by one skilled in the art that electrode stack assembly 225 shown in FIG. 6(*a*) is merely illustrative, and does not limit the scope of the present invention in any way respecting the number or combination of anode sub-assemblies 170, cathode layers 175, separator layers 180, anode tabs 195, cathode tabs 176, and so on. The number of electrode components is instead determined according to the total capacitance required, the total area of each layer, the specific capacitance of the foil employed and other factors.

In another embodiment of electrode stack assembly 225, the number of anode layers 185 employed in each anode subassembly 170 is varied in the stack. Such a design permits the fabrication of capacitors having the same layer area but nearly continuously varying different and selectable total capacitances that a user may determine by increasing or decreasing the number of anode layers 185/190 included in selected anode sub-assemblies 170 (as opposed to adding or subtracting full anode/cathode sub-assemblies 227 from electrode stack assembly 225 to thereby change the total capacitance). Following placing of cathode layer 175*i* in the stack, outer paper layer 165*b* is placed thereon, and outer wrap 115 is folded over the top of electrode stack assembly 225. Wrapping tape 245 then holds outer wrap 115 in place and secures the various components of electrode stack assembly 225 together.

The physical dimensions of separator layers 165 and 180 are most preferably somewhat larger than those of anode sub-assemblies 170 and cathode layers 175 to prevent contact of the electrodes with the case wall or electrical shorting between opposing polarity electrode layers due to the presence of burrs, stray or particulate material, debris or imperfections occurring therein. The reliability and functionality of capacitor 265 may be compromised if a portion of anode sub-assembly 170 comes into contact with a conducting case wall, if a burr on the periphery of anode sub-assembly 170 or cathode layer 175 comes into contact with an adjoining layer of opposing polarity, or if separator layer 180*a* or 180*b* does not provide sufficient electrical insulation between adjoining opposite-polarity electrode layers and conducting particulate matter bridges the gap therebetween.

The additional separator material most preferably disposed about the periphery of electrode stack assembly 225 is referred to herein as separator overhang. Decreasing the amount of separator overhang increases the energy density of capacitor 265. It is beneficial from an energy density optimization perspective, therefore, to decrease the amount or degree of separator overhang. The amount of separator overhang required has been discovered to be primarily a function of the stack-up tolerance characteristic of the stacking method employed.

A preferred method for assuring consistent registration of separator layers 165 and 180, anode sub-assemblies 170 and cathode layers 175 in electrode stack assembly 225 involves stacking the various elements of electrode stack assembly 225 using robotic assembly techniques. More particularly, the various electrode and separator layers of electrode stack assembly 225 are stacked and aligned using an assembly work cell comprising four Seiko 4-axis SCARA Model No. TT8800 and TT8500, or equivalent, to pick up and place the various electrode and separator elements in an appropriate stacking fixture. Other suitable methods for stacking and registering electrode and separator layers include cam driven walking beam assembly machine techniques, rotary table machine techniques, multiple station single stacking machine techniques, and the like.

In a preferred method, a preformed or cut separator, electrode layer or sub-assembly is presented to a robot arm, which then picks the part up with end-of-arm tooling. A Venturi system produces a vacuum in the end-of-arm tooling. The system creates a vacuum at an appropriate time such that the part is sucked up onto the end-of-arm tooling. The vacuum is next released when the part is placed in the stacking fixture. A direct vacuum system, such as rubber suction cups, or other contact or non-contact pick up robotic or manual assembly methods may also be employed. The position of the part is robotically translated from the pickup point into the stacking fixture by the robot arm with an accuracy of 0.005 inch (0.013 mm) or less. After placing the part in the stacking fixture, part alignment is most preferably verified electronically with a SEIKO COGNEX 5400 VISION System, or equivalent, in combination with a SONY XC-75 camera, or equivalent. The camera is mounted on the robot arm to permit the accuracy of part placing to be verified. This system can accurately determine the position of each part or element in electrode stack assembly 225 to within 0.01 millimeters. Once all layers have been placed in the stacking fixture by the robot arm, the stack is presented for wrapping.

The foregoing methods permit precise alignment and stacking of separator layers 165 and 180, anode sub-assemblies 170 and cathode layers 175 in electrode stack assembly 225, while minimizing the addition of undesirable unused volume to capacitor 265.

Another method for assuring registration of separator layers 165 and 180, anode sub-assembly 170 and cathode layer 175 in electrode stack assembly 225 involves alignment elements disposed within the stacking fixture are employed in a manual process which utilizes fixture registration points. In such a method, the stacking fixture has several alignment elements such as posts or side walls disposed about its periphery for positioning separator layers 165 and 180. Because cathode layers 175 and anode sub-assemblies 170 do not extend to the periphery of the separator, an alternative means for accurately positioning those electrodes becomes necessary.

Positioning of alternating cathode layers 175 and anode sub-assemblies 170 is most preferably accomplished using alignment elements such as posts or side walls disposed about the periphery of cathode tab 176 and anode tab 195. It has been discovered that the accuracy of layer placing and positioning is primarily a function of the length of the electrode tabs. The longer the tab, the less significant the alignment error becomes. Electrode tab length must typically be balanced against the loss of electrode material which occurs during die cutting, which in turn results primarily due to the longer length of cathode tab 176 in respect of the length of anode tab 195. Tabs 176 and 195 may include or contain alignment features therein having any suitable geometry for facilitating registration and positioning in respect of alignment elements. Any additional tab length utilized for registration of the electrode layers is most preferably trimmed from electrode stack assembly 225 during the process of electrode tab interconnection (more about which we say below).

Another method for ensuring registration of separator layers 165 and 180, anode sub-assembly 170 and cathode layer 175 in electrode stack assembly 225 does not require the use of internal alignment elements within capacitor 265 is enveloping or covering anode sub-assembly 170 and cathode layer 175 with separator material. In this method, separator layers 180a and 180b are combined into a single die cut piece part that is folded around either anode sub-assembly 170 or cathode layer 175. The free edges of the separator are then secured by doubled-sided transfer tape, another adhesive, stitching or ultrasonic paper welding. Construction of an electrode sub-assembly in this manner secures and registers anode sub-assembly 170 and cathode layer 175 in respect of the periphery of the separator envelope so formed. The resulting anode/cathode sub-assembly 227 is then presented for stacking in electrode stack assembly 225.

Figure 8:
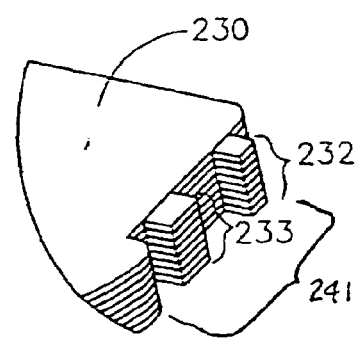
FIG. 8 is an enlarged view of a portion of the electrode stack assembly shown in FIG. 7.
Figure 7:
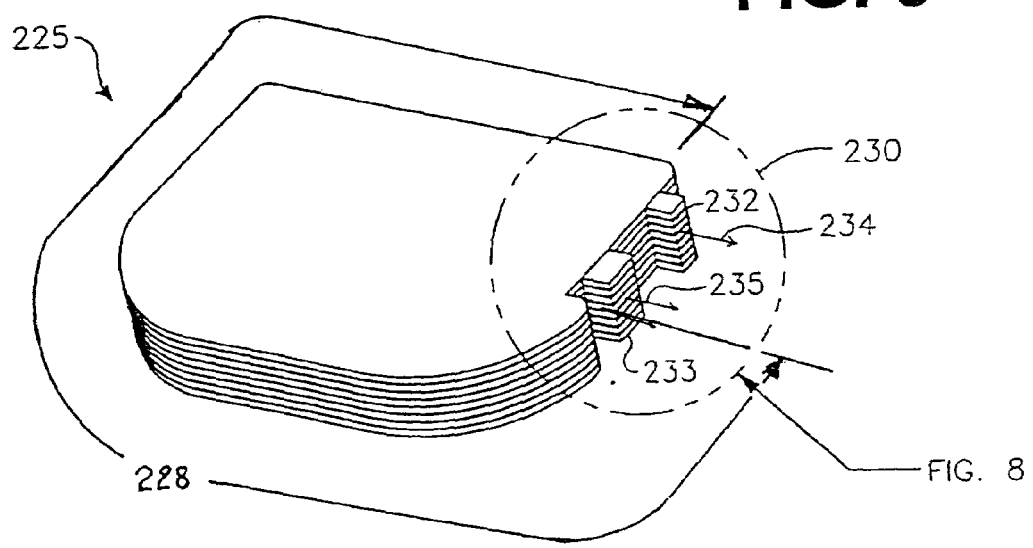
FIG. 7 is a top perspective view of one embodiment of an electrode stack assembly of an electrolytic capacitor incorporating the present invention.

FIG. 7 shows a top perspective view of one embodiment of an electrode stack assembly 225 of the electrolytic capacitor 265. FIG. 8 shows an enlarged view of a portion of the electrode stack assembly 225 of FIG. 7. After wrapping electrode stack assembly 225 with outer wrap 115 and wrapping tape 245, interconnection of gathered anode tabs 232 and gathered cathode tabs 233 with their respective external terminals is most preferably made.

Figure 9:
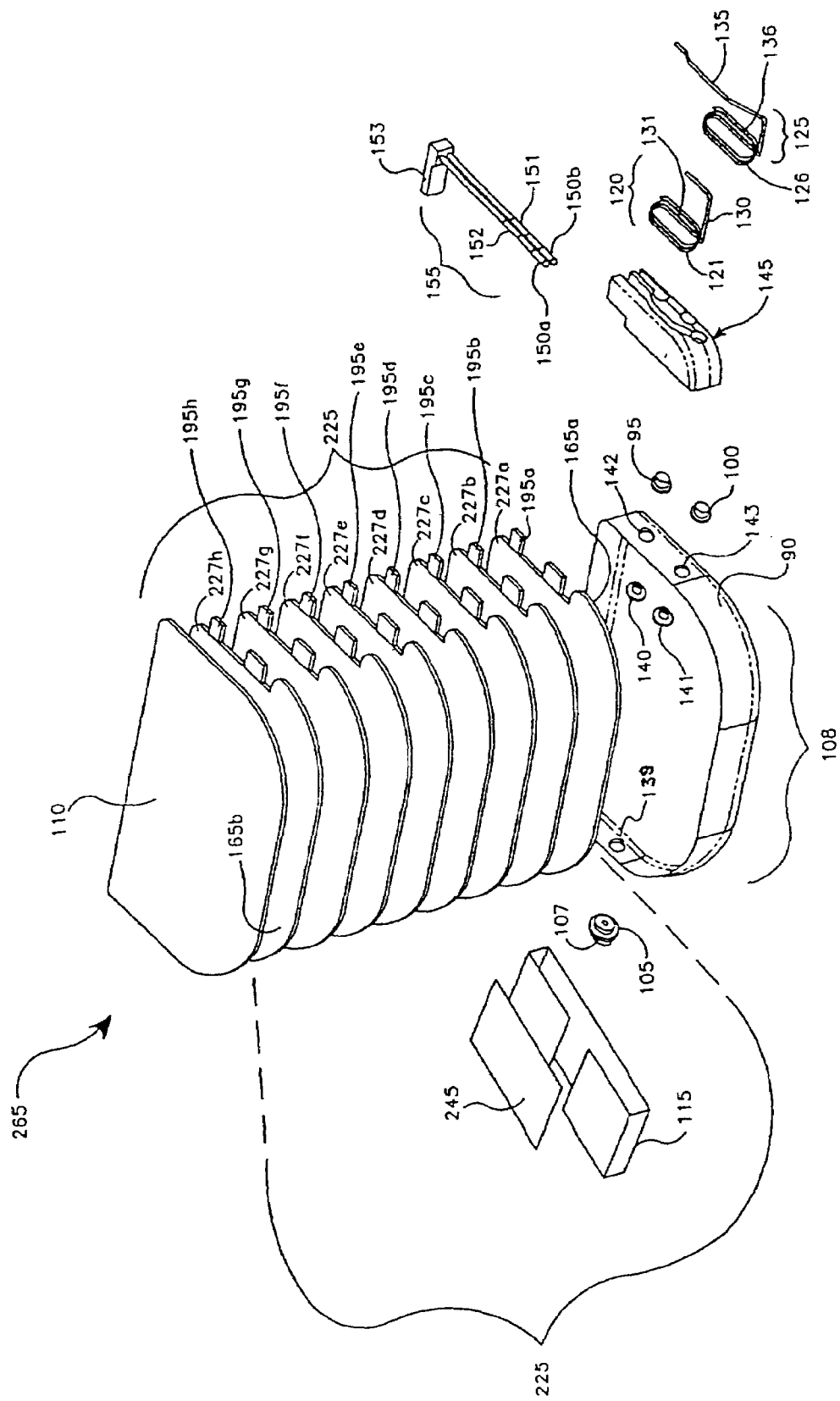
FIG. 9 is an exploded top perspective view of one embodiment of a capacitor of the present invention employing the electrode stack assembly of FIGS. 6, 7 and 8 therein.

FIG. 9 shows an exploded top perspective view of the embodiment of the capacitor 265 employing the electrode stack assembly of FIGS. 6, 7 and 8 therein and not employing a case liner. This embodiment includes anode feedthrough 120 and cathode feedthrough 125 most preferably having coiled basal portions 121 and 126, respectively. Feedthroughs 120 and 125 provide electrical feedthrough terminals for capacitor 265 and gather gathered anode tabs 232 and gathered cathode tabs 233 within basal portions 121 and 126 for electrical and mechanical interconnection.

Figure 10:
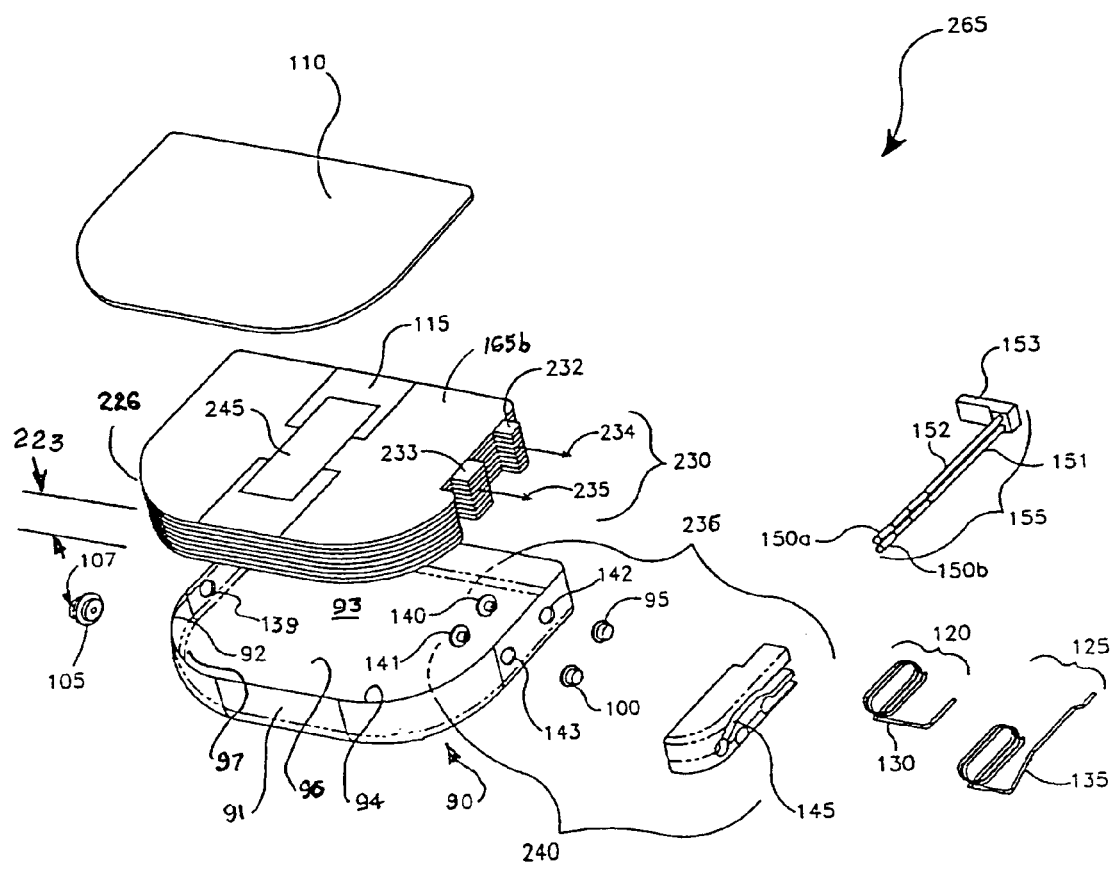
FIG. 10 is an exploded top perspective view of the partially assembled capacitor of FIG. 9.

In one method of making tab interconnections and feedthrough terminal connections, feedthrough wire is first provided for construction of feedthroughs 120 and 125, as shown in FIGS. 9 and 10. In one embodiment, a preferred feedthrough wire is aluminum having a purity greater than or equal to 99.99% and a diameter of 0.020 inch (0.510 mm). Wire is trimmed to predetermined lengths for use in anode feedthrough 120 or cathode feedthrough 125. One end of the trimmed wire is coiled such that its inside diameter or dimension is slightly larger than the diameter or dimension required to encircle gathered anode tabs 232 or gathered cathode tabs 233.

Gathered anode tabs 232 are next gathered, or brought together in a bundle by crimping, and inside diameter 131 of anode feedthrough coil assembly 120 is placed over gathered anode tabs 232 such that anode feedthrough pin 130 extends outwardly away from the base of gathered anode tabs 232. Similarly, gathered cathode tabs 233 are gathered and inside diameter 136 of cathode feedthrough coil assembly 125 is placed over gathered cathode tabs 233 such that cathode feedthrough pin 135 extends outwardly away from the base of cathode tab 233. Coiled basal portions 121 and 126 of anode and cathode feedthroughs 120 and 125 are then most preferably crimped onto anode and cathode tabs 232 and 233, followed by trimming the distal ends thereof, most preferably such that the crimps so formed are oriented substantially perpendicular to imaginary axes 234 and 235 of tabs 232 and 233. Trimming the distal ends may also, but less preferably, be accomplished at other non-perpendicular angles respecting imaginary axes 234 and 235.

A crimping force is applied to feedthrough coils 121 and 126 and tabs 232 and 233 throughout a subsequent preferred welding step. In one method, it is preferred that the crimped anode and cathode feedthroughs be laser or ultrasonically welded along the top portion of the trimmed edge of the distal ends to anode and cathode tabs 232 and 233. Following welding of feedthroughs 120 and 125 to gathered anode tabs 232 and gathered cathode tabs 233, respectively, pins 130 and 135 are bent for insertion through feedthrough holes 142 and 143 of case 90.

Many different embodiments of the feedthroughs, and means for connecting the feedthroughs to anode and cathode tabs exist other than those shown explicitly in the figures. For example, the feedthroughs include embodiments comprising basal portions having open sides, forming "U" or "T" shapes in cross-section, forming a coil having a single turn of wire, forming a coil having three or more turns of wire, formed from flattened wire, or basal portions formed from crimping sleeves or layers of metal for connecting feedthrough pins 130 and 135 to anode and cathode tabs 232 and 233 Various methods of making tab interconnections and feedthrough connections which are not critical to the present invention are disclosed in the above-referenced'133 patent which may be followed in completing the fabrication of capacitor 265.

FIG. 10 shows an exploded top perspective view of capacitor 265 of FIG. 9 in a partially assembled state. Case 90 contains a means for accepting anode ferrule 95 therein, shown in FIGS. 9 and 10 as anode feedthrough hole or opening 142. Case 90 further contains a means for accepting cathode ferrule 100, shown in FIGS. 9 and 10 as cathode feedthrough hole or opening 143. Case 90 also includes a means for accepting fill port ferrule 105, shown in FIGS. 9 and 10 as fill port hole 139. In a preferred embodiment, case 90 and cover 110 are formed of aluminum and are electrically connected to the cathode layers, and where case 90 and cover 110 are at the same electrical potential as the cathode layers, i.e., at negative potential.

Ferrules 95, 100 and 105 are most preferably welded to case 90 (or otherwise attached thereto such as by a suitable epoxy, adhesive, solder, glue or the like), and together comprise case sub-assembly 108. Radial flanges in anode ferrule 95 and cathode ferrule 100 provide a region for making a lap joint between the side wall of case 90 and around the perimeters of feedthrough ferrule holes 142 and 143. In preferred methods, a circumferential laser weld is made in the circumferential joint between the ferrules and the case side wall 92, and welding is carried out in two primary steps. First, a series of tack welds is made around the circumference of the joint. The tack welds are most preferably made either by making adjoining, successive tack welds around the perimeter or by making a first tack weld at a first location along the perimeter, making a second weld diametrically opposed from the first weld along the perimeter, making a third weld adjacent to the first weld, making a fourth weld adjacent to the second weld, and so on. Finally, a final closing weld is made around the hole perimeter to hermetically seal tack welded joint 93.

Wire guides 140 and 141 center pins within the inside diameter of the ferrules to permit anode and cathode pins 130 and 135 to be electrically insulated from the inside surface of case 90, anode ferrule 95, and cathode ferrule 100. Wire guides 140 and 141 may themselves be electrically insulating, and electrical insulation of pins 130 and 135 from case 90 and other components is most preferably enhanced by means of potting adhesive 160.

Wire guides 140 and 141 most preferably contain annular, ramped, or "snap-in" features formed integrally therein. Those features prevent wire guides 140 and 141 from being pushed out of their respective ferrules during handling, but are most preferably formed such that insertion of wire guides 140 and 141 in their corresponding ferrules may occur using forces sufficiently low so as not to damage case 90 or ferrules 95 or 100 during the inserting step.

Wire guides 140 and 141 may be formed from any of a wide variety of electrically insulating materials that are stable in the environment of an electrolytic capacitor. In one preferred embodiment, the material from which wire guides 140 and 141 is made is an injection molded polysulfone known as AMOCO UDEL supplied by Amoco Performance Products of Atlanta, Ga. In other embodiments, wire guides 140 and 141 may be formed from other chemically resistant polymers such as fluoroplastics (e.g., ETFE, PTFE, ECTFE, PCTFE, FEP, PFA or PVDF), fluoroelastomers, polyesters, polyamides, polyethylenes, polypropylenes, polyacetals, polyetherketones, polyarylketones, polyether sulfones, polyphenyl sulfones, polysulfones, polyarylsulfones, polyetherimides, polyimides, poly(amideimides), PVC, PVDC-PVC copolymers, CPVC, polyfurans, poly(phenylene sulfides), epoxy resins, silicone elastomers, nitrile rubbers, chloroprene polymers, chlorosulfonated rubbers, polysulfide rubbers, ethylene-polypropylene elastomers, butyl rubbers, polyacrylic rubbers, fiber-reinforced plastics, glass, ceramic and other suitable electrically insulating, chemically compatible materials.

As used in the specification and claims hereof, the foregoing acronyms have the following meanings: the acronym "ETFE" means poly(ethylene-co-tetrafluoroethylene); the acronym "PTFE" means polytetrafluoroethylene; the acronym "CTFE" means poly(ethylene-co-chlorotrifluoroethylene); the acronym "PCTFE" means polychlorotrifluoroethylene; the acronym "FEP" means fluorinated ethylene-propylene copolymer; the acronym "PFA" perfluoroalkoxy fluoropolymer; the acronym "PVDF" means polyvinylidene fluoride; the acronym "PVC" means polyvinyl chloride; the acronym "PVDC-PVC" means polyvinylidene chloride—polyvinyl chloride copolymer; and the acronym "CPVC" means chlorinated polyvinyl chloride.

A preferred material for forming connector block 145 is an injection molded polysulfone known as AMOCO UDEL supplied by Amoco Performance Products of Atlanta, Ga. Connector block 140 may also be formed from any suitable chemically resistant thermoplastic polymers such as a fluoroplastic (e.g., ETFE, PTFE, ECTFE, or PCTFE, FEP, PFA, PVDF), polyester, polyamide, polyethylene, polypropylene, polyacetal, polyarylketone, polyether sulfone, polyphenyl sulfone, polysulfone, polyarylsulfone, polyetherimides, polyimide, poly(amide-imide), PVC, PVDC-PVC copolymer, CPVC, polyfuran, poly(phenylene sulfide), epoxy resin and fiber reinforced plastic.

In one embodiment, connector block 145 is placed on anode ferrule 95 and cathode ferrule 100 by guiding anode feedthrough pin 130 through connector block anode feedthrough hole 300, and then guiding cathode feedthrough pin 135 through connector block cathode feedthrough hole 305. Connector block 145 is next seated flush against the exterior surface of case 90. Anode feedthrough pin 130 is then inserted into anode crimp tube 150b of wire harness 155. Cathode feedthrough pin 135 is then inserted into cathode crimp tube 150a of wire harness 155. Crimp tubes 150a and 150b are then crimped to feedthrough pins 130 and 135.

In other preferred embodiments, electrical connections in connector block 145 may be established using techniques such as ultrasonic welding, resistance welding and laser welding. In such joining techniques, the joint geometry may also be a cross-wire weld between feedthrough wire 130 or 135 and harness wire 151 or 152.

The distal or basal portions of crimp tubes 150a and 150b are crimped on insulated anode lead 151 and insulated cathode lead 152, respectively. Insulated leads 151 and 152 are likewise connected to terminal connector 153. Terminal connector 153 may most preferably be connected to electronics module 360. Standard methods of making aluminum electrolytic capacitors do not lend themselves readily to very small crimp connections, especially in miniaturized ICD designs. A preferred method permits small crimp connections and interconnection means to be formed, and further permits highly efficient packaging in ICD IPG 10.

In the preferred method described above, connector block 145 and epoxy adhesive provide strain relief to feedthrough pins 130 and 135 and to the feedthrough wire crimp connections, and further provide an epoxy seal between wire guides 140 and 141, case 90 and ferrules 95 and 100. The crimp tubes may also serve as a connection point for device level assembly. Alternatively, the crimp tubes may be integrated within wire harness 155 prior to capacitor assembly. The wire harness may then serve as a means of routing capacitor electrical connections as desired in, for example, device level assembly steps. In the embodiment shown in FIGS. 10 and 11, terminal connector 153 forms the female end of a slide contact. In another embodiment, terminal connector 153 is connected to other modules by resistance spot welding, ultrasonic wire bonding, soldering, crimping, or other attachment means.

The particular configuration and fabrication of the feedthroughs, the connections thereto, the connector block, the wire harness, etc., are not important to the present invention. Further details related to the fabrication of the depicted, exemplary form of the feedthroughs, internal and external connections thereto, the connector block, the wire harness, etc., are set forth in detail in the above-referenced '133 patent.

Figure 11:
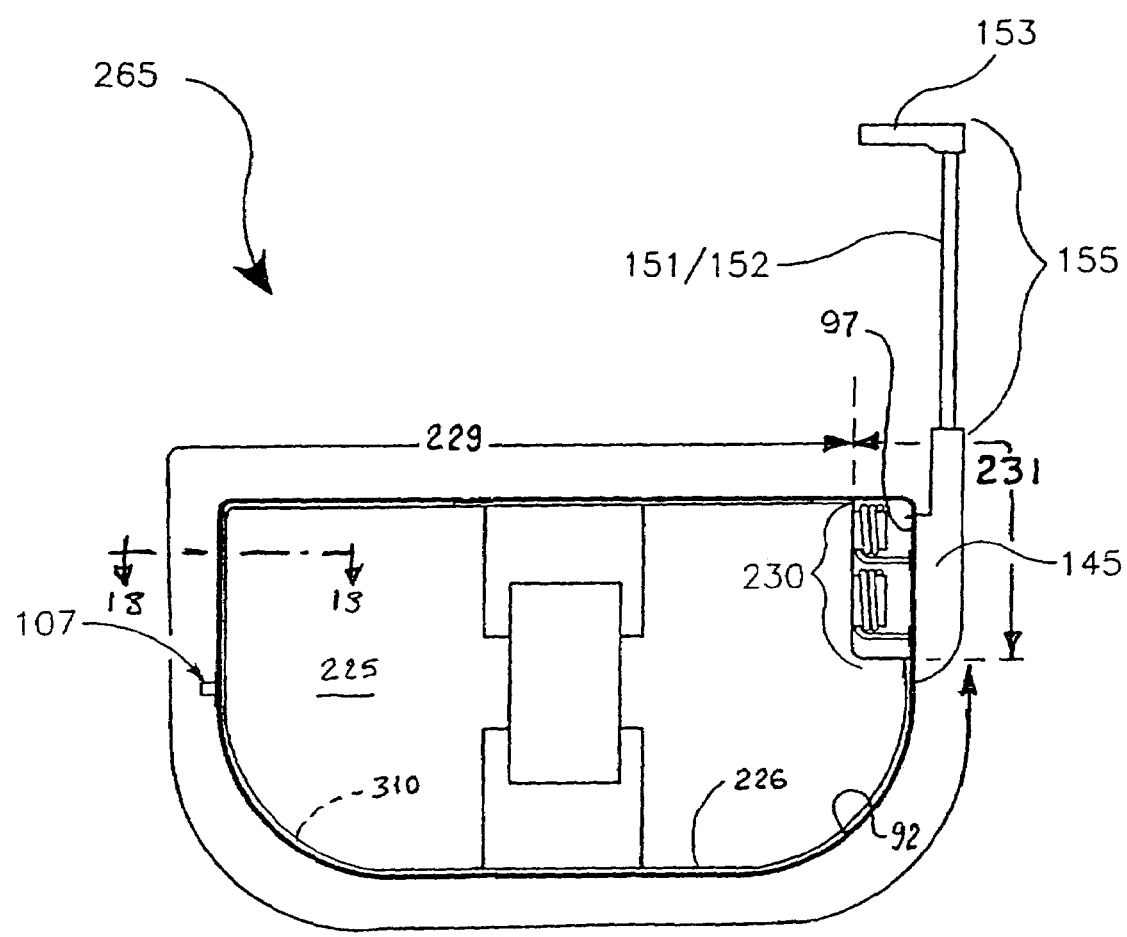
FIG. 11 is a top view of one embodiment of a partly assembled capacitor of the present invention having no cover disposed thereon.
Figure 12:
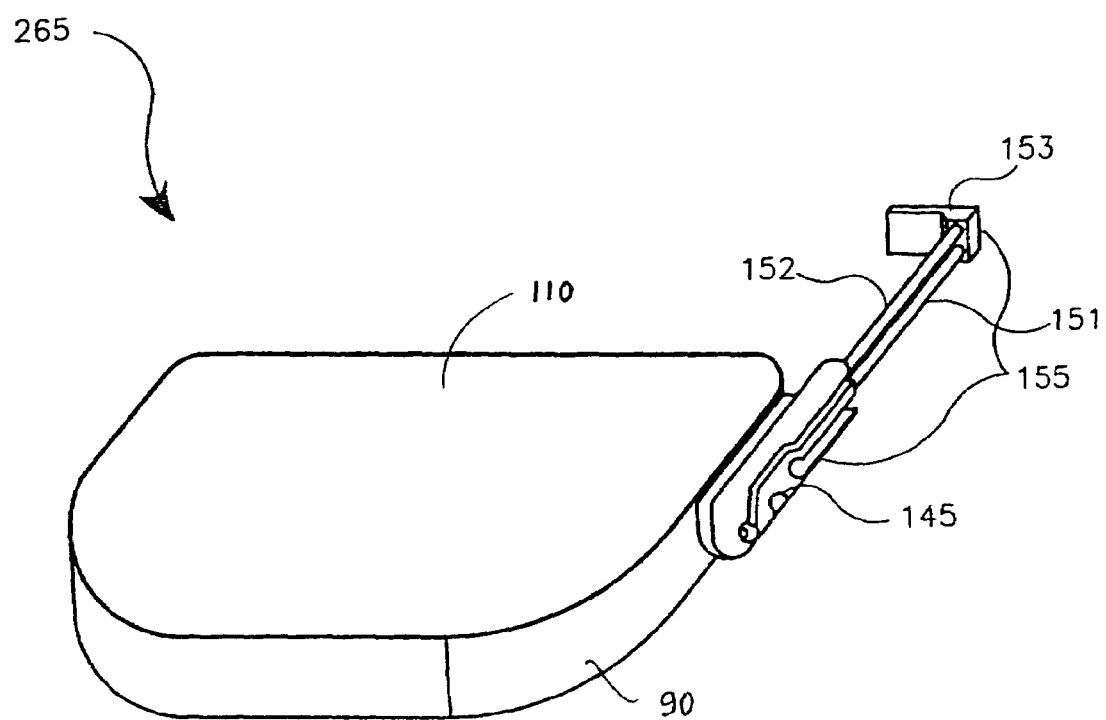
FIG. 12 is a top perspective view of the capacitor of FIG. 11 having a cover disposed thereon.

FIG. 11 shows a top view of one embodiment of assembled capacitor 265 with cover 110 not present and without a case liner separating electrode stack assembly 225 from the case 90 and cover 110. In one embodiment, the head space portion of electrode stack assembly 225 (referred to herein as head space 230) is insulated from case 90 and cover 110. The means by which head space insulation may be provided include molded, thermally-formed, die cut, or mechanically formed insulating materials and means, where the materials and means are stable in the environment of an electrolytic capacitor. Suitable materials from which head space insulators may be formed include all those listed hereinabove respecting materials for forming wire guides 140 and 141. Another means of providing head space insulation is to wrap electrically insulating tape, similar to wrapping tape 245, around head space 230 to prevent the anode or cathode terminals from contacting case 90 or cover 110 or each other. Various crimp and joint configurations for joining the cover 110 to case 90 are described in detail in the above-referenced, commonly assigned '133 patent. In accordance with one aspect of the present invention, the head space insulation may be provided by a case liner 300 described further below. FIG. 11 may also include a lower half section 310 of the case liner 300 described below (not visible in FIG. 11) that the electrode stack assembly 225 is nested into. An upper half section would be fitted over the electrode stack assembly after completion of the above-described electrical connections for connecting feedthrough pins 130 and 135 to anode and cathode tabs 232 and 233.

After all welding steps are completed, the interior case chamber of capacitor 265 is filled with electrolyte through fill port 107 welded into a hole 139 in the side wall of the capacitor case 90, the capacitor is aged, the fill port lumen is closed and the capacitor is tested. The capacitor aging, the fill port construction, use in filling the capacitor interior case with electrolyte and the closure of the fill port lumen are not critical to the present invention, and examples of the same are disclosed in detail in the above-referenced, commonly assigned '133 patent. Applications in implantable defibrillators may require two capacitors 265 to be connected in series. In this embodiment, an insulator is provided by a two sided adhesive being disposed between the capacitors 265 so that they are joined along opposing faces with the insulator/adhesive strip disposed therebetween. The pair of capacitors 265 is then provided for assembly in ICD IPG 10 as shown and described above with respect to FIGS. 3(a) through 3(g).

In accordance with one aspect of the present invention, the capacitor case sub-assembly 108 and the case cover 110 of FIG. 9 define an interior case chamber 93 when hermetically welded together at the case side wall upper edge as described above. The case 90 has a base 96 bounded by a base peripheral edge at the junction of the base 96 and side wall 91 extending upwardly at a right angle therefrom to a case opening edge 94 for receiving cover 110 whereby the interior case chamber has a case chamber periphery 97 corresponding in shape to the base peripheral edge and bounded by the interior case side wall surface 92.

The electrode stack assembly 225 located within the interior case chamber 93 is dimensioned to have a stack periphery 226 configured in mating relation with the case chamber periphery defined by the interior case side wall surface 92 as shown in FIGS. 10, 11, 13(a) and 13(b). As described above, the electrode stack assembly 225 comprises a plurality of capacitor layers 227a–227h and lower and upper separator layers 165a and 165b. The capacitor layers 227a–227h and separator layers 165a and 165b are stacked in registration upon one another and between the case base 96 and the cover 110 through a stack height 223. Edge portions of two capacitor layers 227b and 227c are shown without a liner in FIG. 13(a) and with a case liner 300 in FIG. 13(b).

Figure 13A:
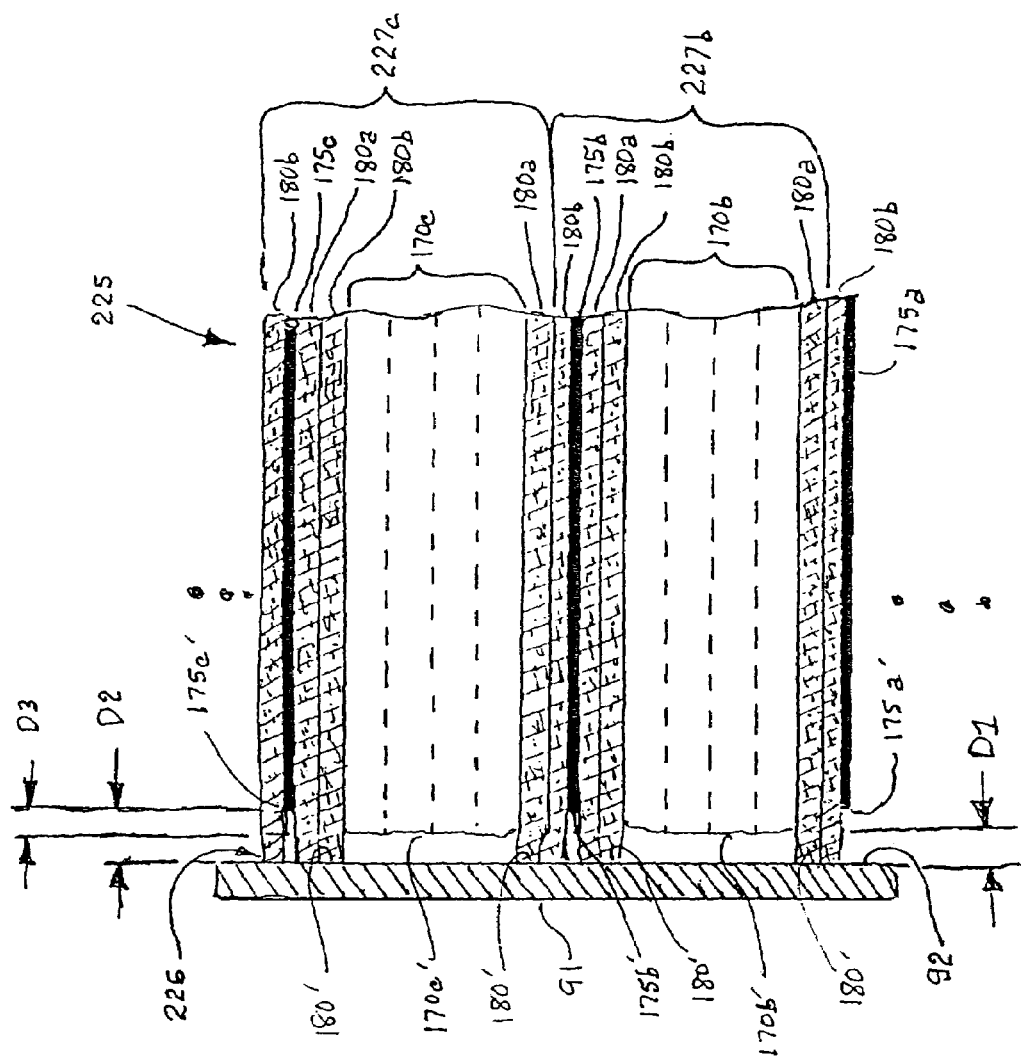
FIG. 13(a) is a partial cross-section view of the case periphery and electrode stack periphery taken along lines 13—13 of FIG. 11 depicting peripheral edges of anode sub-assemblies, cathode layers, and separator layers of a portion of the stack height of the electrode stack assembly.
Figure 13B:
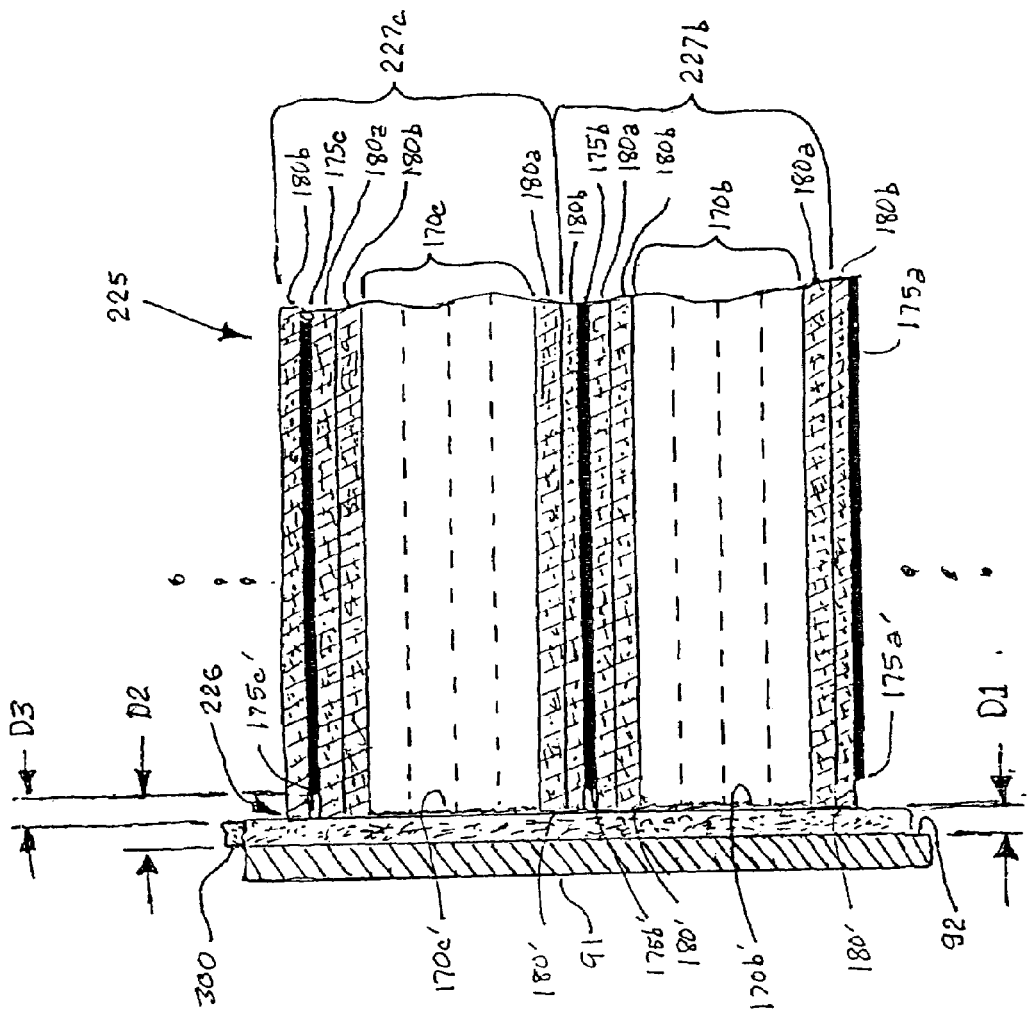
FIG. 13(b) is a partial cross-section view taken along lines 13—13 of FIG. 11 of the case periphery and electrode stack periphery along with a case liner of the type depicted in FIGS. 14 and 15 depicting peripheral edges of anode subassemblies, cathode layers, and separator layers of a portion of the stack height of the electrode stack assembly.

As described above with respect to FIG. 4, and as shown in FIGS. 13(a) and 13(b), each capacitor layer 227a–227h comprises a cathode layer 175a–175h having a cathode peripheral edge 175a'–175h' extending toward the interior case side wall 92 throughout a major portion 229 of the case chamber periphery 97 (FIG. 11) and having a cathode tab 176a–176h extending in the head space 230 toward the case side wall 92 in a minor portion 231 of the case chamber periphery 97. Thus, the stack periphery 226 similarly consists of a major periphery length 229 corresponding to major portion 229 and a minor periphery length 241 corresponding to minor portion 231 at the head space 230 as shown in FIGS. 7 and 8. The stack periphery 226 is closely spaced from and configured in shape through the major periphery length 228 to the shape of the major portion 229 of the case chamber periphery 97.

Each capacitor layer 227a–227h also includes an anode sub-assembly 170a–170h comprising at least one anode layer 185 and/or 190 having an anode sub-assembly peripheral edge 170a'–170h' extending toward the case side wall 92 throughout the major portion 229 and having an anode tab 195a–195h extending in the head space 230 toward the case side wall interior surface 92 in the minor portion 231 of the case chamber periphery 97.

Each capacitor layer 227a–227h also includes the electrolyte bearing inner separator layer 180 formed of two separator layer sheets 180a and 180b as depicted in FIGS. 4, 13(a) and 13(b). Each separator layer 180 has a separator peripheral edge 180' extending toward the interior case side wall 92. The separator layers 180 disposed between each adjacent anode sub-assembly and cathode layer electrically separates each anode sub-assembly from each adjacent cathode layer of the stacked capacitor layers In reference to the embodiment of FIG. 13(*a*), it is preferred to cut or otherwise form separator layer 180 such that its outer periphery edge 180' is the outermost surface of the stack periphery 226 and conforms closely to that of the case chamber periphery 97 so that the outer peripheral edges 180' contact the adjacent interior side wall surface 92 In preferred embodiments, the periphery of separator layer is disposed within ±0.009 inches of the adjoining side wall surface 92. Such close conformity between the periphery edge 180' and the corresponding internal side walls of case 90 has been discovered to provide the advantage of permitting separator layers 180 to immobilize or secure firmly in place electrode stack assembly 225 in case 90. This immobilization occurs because the separator paper forming separator layers 180 swells after electrolyte is added through the lumen of fill port 107 into the interior case chamber 93 of the otherwise assembled and sealed capacitor 265.

Further in reference to FIG. 13(*a*), in each capacitor layer 227*b*, 227*c*, et seq., the anode sub-assembly peripheral edges 170*b'*, 170*c'*, et seq., are disposed at a first distance D1 from the separator layer peripheral edges 180' and the case interior side wall surface 92 throughout the major portion 229 of the case chamber periphery 97. The cathode peripheral edges 175*a'*, 175*b'*, 175*c'*, et seq., are disposed at a second distance D2 from the case interior side wall surface 92 and the separator layer peripheral edges 180' throughout the major portion 229 of the case chamber periphery 97. In this example, the second distance D2 is greater than the first distance D1, and a separation difference distance D3=D2−D1. The distance D1 is preferably on the order of about 0.015 to 0.040 inches (0.381 to 1.016 mm).

The distance D2 is preferably on the order of about 0.030 to 0.040 inches (0.762 to 1.016 mm). The distance D3 is preferably on the order of about 0.000 to 0.015 inches (0.000 to 0.381 mm).

In the embodiment of FIG. 13(*a*), the distance D1 constitutes "separator overhang". Decreasing the amount of separator overhang increases the total amount of "active" electrode material available and the resulting energy density of a given capacitor design. It is beneficial from an energy density optimization perspective, therefore, to decrease the amount or degree of separator overhang. The amount of separator overhang required has been discovered to be primarily a function of the stack-up tolerance characteristic of the stacking method employed. In known cylindrical capacitors, we discovered that the amount of separator overhang is typically on the order of 0.100 inches (2.5 mm).

In the embodiment depicted in FIG. 13(*b*), a side wall of an electrically insulating case liner 300 is interposed between the interior side wall surface 92 and the anode sub-assembly peripheral edges 170*b'*, 170*c'*, et seq., the separator layer peripheral edges 180', and the cathode layer peripheral edges 175*a'*, 175*b'*, 175*c'*, et seq. In this embodiment, the case liner side wall occupies the distance D1, and the separator layer peripheral edges 180' and the anode sub-assembly peripheral edges 170*b'*, 170*c'*, et seq., are all at about the distance D1 from the side wall interior surface 92. Preferably, distance D3 ranges from 0.050 to 0.100 inches (0.125 to 0.250 mm) more preferably from 0.005 to 0.050 inches (0.013 to 0.125 mm), allowing for maximization of the size of the anode and cathode layers of electrode stack assembly 225. The separation difference distance D3 remains at D3=D2−D1. But, in this embodiment, D1 can be made much thinner, in the range of about 0.001 to 0.100 inches (0.025 to 0.254 mm) and more preferably in the range of about 0.003 to 0.005 inches (0.075 to 0.127 mm). Therefore, the anode layers can be made larger, increasing energy storage capacity by about 4%.

In these ways, the anode layer peripheral edges of the anode sub-assemblies 170*a*–170*h* of the stacked capacitor layers 227*a*–227*h* extend closer to the case interior side wall surface 92 than the cathode layer peripheral edges 175*a'*–175*h'* throughout the major portion 229 of the case chamber periphery 97. The tendency of any individual peripheral edges of the outermost anode layers of the anode sub-assembly peripheral edges 170*a'*–170*h'* to extend toward an adjacent cathode layer peripheral edge 175*a'*–175*h'* in the stack height direction causes the anode layer edges having such tendency to contact an adjacent anode layer, not an intervening cathode layer. Therefore, any such edge distortion that is present or any edge burrs or debris present at the anode layer edges merely causes the anode layers to contact one another, and electrical shorting of the anode and cathode layers is avoided.

Figure 14:
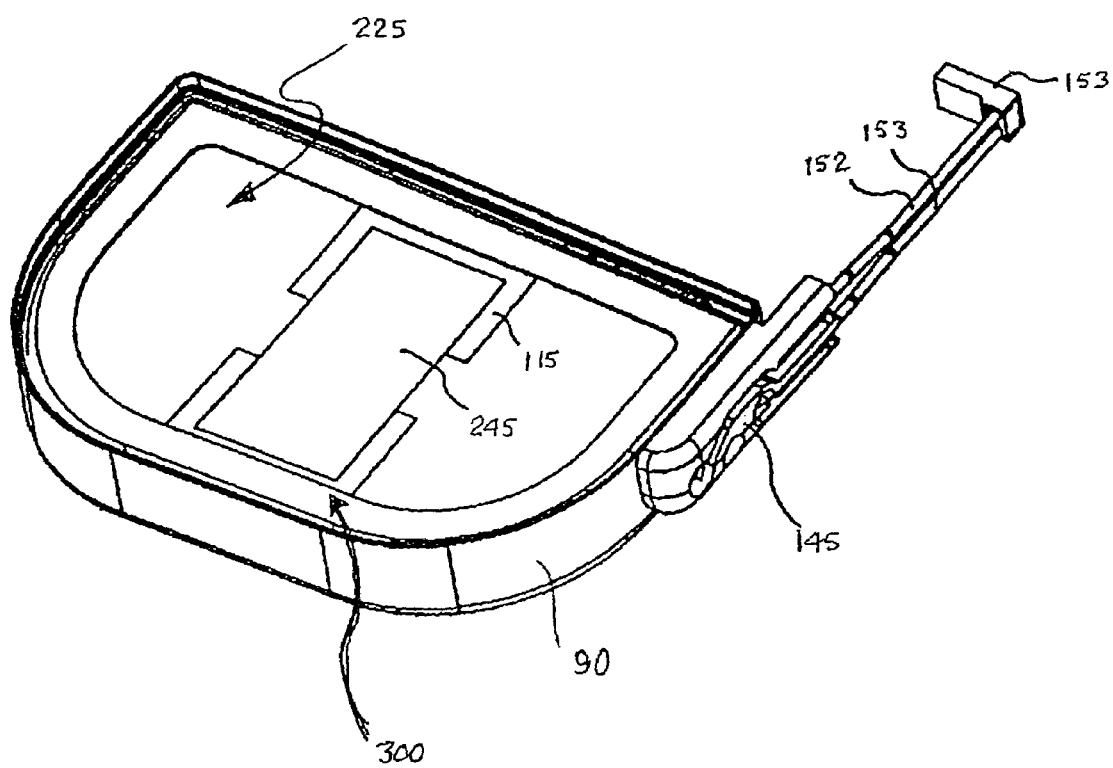
FIG. 14 is a perspective view of one embodiment of a fully assembled capacitor of the present invention having a case liner and no cover disposed thereon.

FIG. 14 shows a top view of such an embodiment of assembled capacitor 265 with cover 110 not present and with a case liner 300 separating electrode stack assembly 225 from the case 90 and cover 110. The case liner 300 provides an insulating barrier positioned about electrode stack assembly 225 to cover the stack periphery 226 throughout the major portion 229 illustrated in FIG. 9 and to also cover an edge portion of the outer separator layers 165*a* and 165*b*. Wiring harness connector block 145 is coupled to the electrode stack 108 through case 90 as described above.

Figure 15:
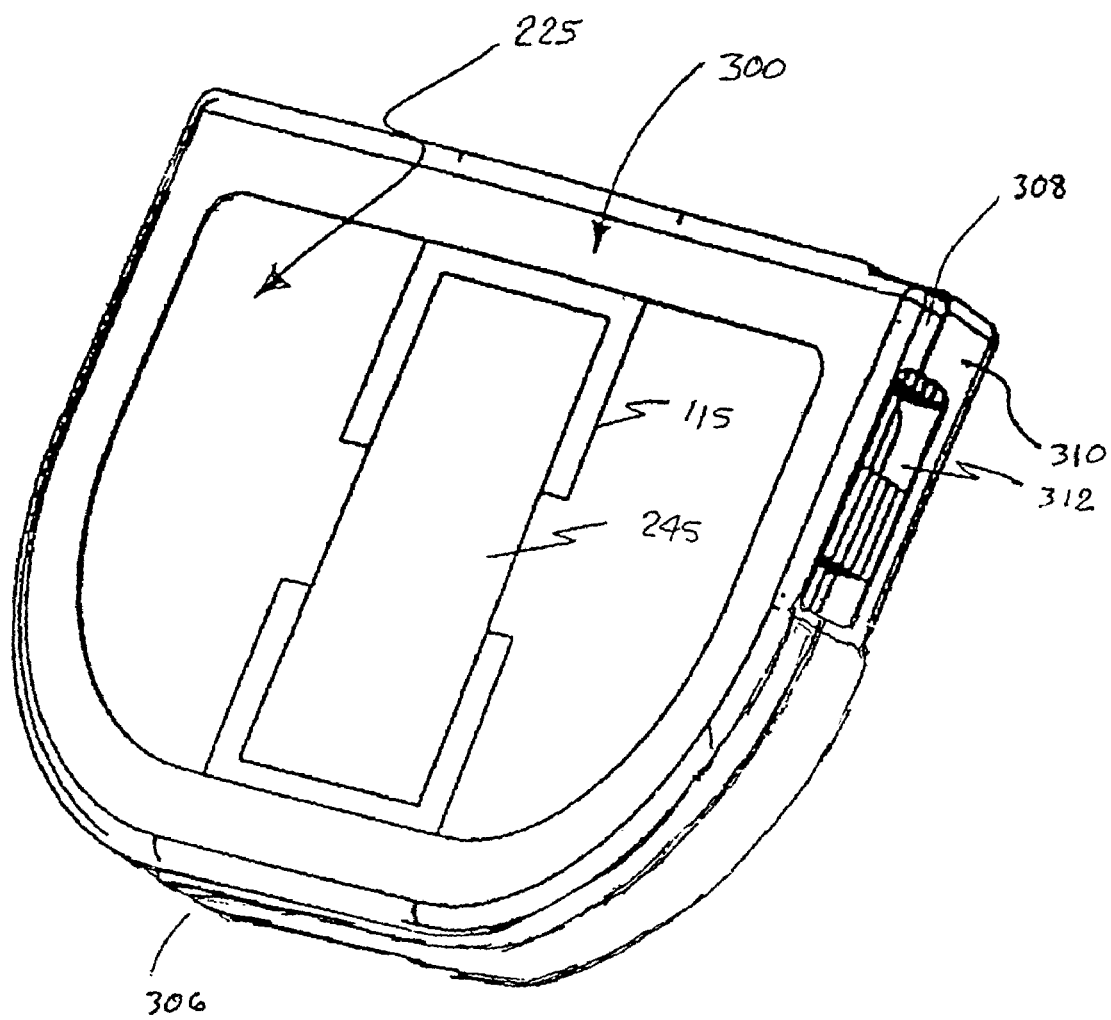
FIG. 15 is a perspective view of the case liner of FIG. 14 placed around the periphery of the electrode stack assembly.

FIG. 15 illustrates case liner 300 as used in FIG. 14 to enclose electrode stack assembly 225. In this illustrated embodiment, case liner 300 is constructed in an upper half section 308 and a lower half section 3 10. Electrode stack assembly 225 is positioned within the upper and lower half sections 308 and 310 in the assembly depicted in FIG. 15. A case liner side wall 306 that extends throughout the major portion 229 illustrated in FIG. 9 is formed when the assembly depicted in FIG. 15 is completed. A cut out section 312 is made in the case liner side wall 306 in the minor portion 231 of the case chamber periphery 97 shown in FIG. 11 to facilitate electrical connections from the feedthrough pins 130 and 135 to anode and cathode tabs 232 and 233, respectively. The electrical connections are made after the liner lower half section 310 is placed in the interior case chamber 93 and the electrode stack assembly is nested into the lower half section as in FIG. 11. The electrical connections illustrated in FIGS. 9–11 are completed, and the upper case liner half section 308 is placed over the upper surface of the electrode stack assembly. A further cut-out hole is provided in the upper and lower half sections 308 and 310 in alignment with the fill port 107 to allow leak testing and introduction of the electrolyte as described, for example, in the above-referenced '133 patent.

Case liner 300 is made of an appropriate thickness of electrically insulating material depending upon the mechanical design of electrode stack assembly 225, the amount of separator layer overhang, the desired distance D1 separation between electrode stack periphery 226 and the case side wall surface 92, etc. In one embodiment liner wall thickness is in the range of 0.001 to 0.100 inches (0.025 to 0.254 mm) and more preferably in the range of 0.003 to 0.005 inches (0.075 to 0.127 mm). Liner wall thickness is also a function of the type of insulating material from which liner 300 is made.

In one embodiment, liner 300 is made of a polymeric material or polymeric blend of materials, and in one preferred embodiment the polymeric material is polysulfone. Other suitable polymeric materials include polypropylene, polyethylene and ETFE. Optionally, liner 300 can be formed of other insulating materials, such as those materials previously disclosed herein for construction of the wire guides 140 and 141. Liner 300 acts as a separator between the electrode stack periphery 226 and case side wall surface 92, and therefore could be made of porous materials or made porous, e.g., by having holes therethrough. Other suitable electrical non-conducting materials for liner 300 will become apparent to those skilled in the art after reading the present application.

The mechanical design of the liner 300 may take many different configurations depending upon the configuration of the electrode stack assembly 225. In applications where the desired shape of capacitor assembly 64 has a low thickness to width aspect ratio, a stacked plate electrode 108 design is preferred to achieve optimal energy density. Liner 300 can be constructed of a single part, a two part assembly, or optionally made with multiple component construction. Various embodiments of liner 300 mechanical design are described in detail in the above-referenced parent patent application Ser. No. 09/531,352. The use of liner 300 extends to cylindrical or other capacitor assembly 64 shapes. Although liner 300 is preferably thermoformed or molded, in another preferred embodiment liner 300 can be coated or deposited on the inside of case 100 or upon electrode stack assembly 225. In this embodiment, the liner 300 is preferably less than 0.050 inches (0.127 mm) and more preferably less than 0.001 inches (0.025 mm), and more preferably less than 0.0005 inches (0.0013 mm) thick.

Although only a few exemplary embodiments of a capacitor 265 in which the present invention is advantageously implemented have been described in detail above, those skilled in the art will appreciate readily that many modifications are possible in the exemplary embodiments without materially departing from the novel teachings and advantages of the invention. Accordingly, all such modifications are intended to be included within the scope of the present invention as defined in the following claims.

The preceding specific embodiments are illustrative of a capacitor structure and method of fabrication thereof and its incorporation into an IMD in accordance with preferred embodiments of the present invention. It is to be understood, therefore, that other expedients known to those skilled in the art or disclosed herein, and existing prior to the filing date of this application or coming into existence at a later time may be employed without departing from the invention or the scope of the appended claims. In the claims, means-plus-function clauses are intended to cover the structures described herein as performing the recited function and not only structural equivalents but also equivalent structures.

All patents and printed publications disclosed herein are hereby incorporated by reference herein into the specification hereof each in its respective entirety.

We claim:

1. A capacitor comprising:
 a case chamber;
 an electrode stack assembly disposed within the case chamber, the electrode stack assembly includes a layer, the layer comprises:
  an anode subassembly comprising at least one anode layer having an anode edge disposed at a first distance from an interior wall of the case chamber; and
  a capacitor layer which includes a cathode edge disposed at a second distance from the wall interior, the second distance greater than the first distance.

* * * * *